(12) United States Patent
Kasashima et al.

(10) Patent No.: US 7,815,939 B2
(45) Date of Patent: Oct. 19, 2010

(54) COATED FINE PARTICLES CONTAINING DRUG FOR INTRABUCCALLY FAST DISINTEGRATING DOSAGE FORMS

(75) Inventors: Yuki Kasashima, Tokyo (JP); Ippei Kurimoto, Tokyo (JP); Hitoshi Kawai, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 0 days.

(21) Appl. No.: 11/458,582

(22) Filed: Jul. 19, 2006

(65) Prior Publication Data

US 2007/0231399 A1    Oct. 4, 2007

Related U.S. Application Data

(60) Provisional application No. 60/701,139, filed on Jul. 20, 2005.

(51) Int. Cl.
*A61K 9/24* (2006.01)
*A61K 9/16* (2006.01)

(52) U.S. Cl. ...................................... 424/471; 424/497

(58) Field of Classification Search ........................ None
See application file for complete search history.

(56) References Cited

U.S. PATENT DOCUMENTS

| | | | |
|---|---|---|---|
| 4,870,059 A | 9/1989 | Mitsuhashi et al. | |
| 5,075,114 A | 12/1991 | Roche | |
| 5,082,669 A | 1/1992 | Shirai et al. | |
| 5,260,072 A | 11/1993 | Roche et al. | |
| 5,534,534 A | 7/1996 | Makino et al. | |
| 5,607,697 A | 3/1997 | Alkire et al. | |
| 5,997,903 A * | 12/1999 | Dietrich et al. | 424/482 |
| 6,011,062 A | 1/2000 | Schneider et al. | |
| 6,017,927 A | 1/2000 | Takeuchi et al. | |
| 6,221,402 B1 | 4/2001 | Itoh et al. | |
| 2002/0119196 A1 | 8/2002 | Parikh et al. | |
| 2002/0155156 A1 | 10/2002 | Mulye | |
| 2003/0096791 A1 | 5/2003 | Gupte et al. | |
| 2004/0136915 A1 | 7/2004 | Dugger et al. | |
| 2004/0138253 A1 | 7/2004 | Slatter | |
| 2004/0198822 A1 | 10/2004 | Fraser et al. | |
| 2005/0175689 A1 * | 8/2005 | Kurimoto et al. | 424/464 |
| 2005/0181031 A1 | 8/2005 | Saito et al. | |
| 2005/0239890 A1 | 10/2005 | Fraser et al. | |
| 2006/0035923 A1 | 2/2006 | Van Meeteren et al. | |
| 2007/0270459 A1 | 11/2007 | Van Meeteren et al. | |
| 2008/0039516 A1 | 2/2008 | Sugihara et al. | |
| 2008/0103171 A1 | 5/2008 | Umejima et al. | |

FOREIGN PATENT DOCUMENTS

| | | |
|---|---|---|
| CN | 1171109 A | 1/1998 |
| EP | 0121291 A2 | 10/1984 |
| EP | 0 459 695 A1 | 5/1991 |
| EP | 0 473 431 A1 | 8/1991 |
| EP | 0459695 A1 | 12/1991 |
| EP | 0473431 A1 | 3/1992 |
| EP | 0801067 A1 | 10/1997 |
| EP | 1 219 291 A1 | 7/2002 |
| EP | 1552825 A1 | 7/2005 |
| EP | 1714965 A1 | 10/2006 |
| EP | 1726304 A1 | 11/2006 |
| EP | 1 728 791 A1 | 12/2006 |
| EP | 1 832 288 A1 | 9/2007 |
| EP | 1 219 291 B1 | 8/2008 |
| JP | 62-136240 A | 6/1987 |
| JP | 5-194218 A | 8/1993 |
| JP | H06-219939 | 8/1994 |
| JP | 9-71764 | 3/1997 |
| JP | 9-110698 A | 4/1997 |
| JP | 10-7547 A | 1/1998 |
| JP | 2003-261439 A | 9/2003 |
| JP | 2004-26675 A | 1/2004 |
| JP | 2004-175796 A | 6/2004 |
| RU | 2 090 567 C1 | 9/1997 |
| RU | 2 136 685 C1 | 9/1999 |
| WO | WO 96/20194 A1 | 7/1996 |
| WO | WO 98/30209 A1 | 7/1998 |
| WO | WO 02/096392 A1 | 12/2002 |
| WO | WO 03/006019 A1 | 1/2003 |
| WO | WO 03/099268 A1 | 12/2003 |

(Continued)

OTHER PUBLICATIONS

Office Action dated Nov. 2, 2009 for Russian Patent Application No. 2007128815/15(031373) corresponding to US2008039516 and US2008103171.

(Continued)

*Primary Examiner*—Michael G Hartley
*Assistant Examiner*—Paul Dickinson
(74) *Attorney, Agent, or Firm*—Townsend and Townsend and Crew LLP

(57) ABSTRACT

Regarding an object of sufficient suppression of unpleasant taste in the oral cavity and quick dissolution in the gastrointestinal tract, which is generated when a drug having a strong unpleasant taste such as bitterness, astringency and the like is applied to a quickly disintegrating preparations in the oral cavity, this invention has achieved the aforementioned object for the first time by employing a constitution of coating a coat of a water-soluble polymer and a specified ratio of a pH-independent water-insoluble polymer and hydroxypropylcellulose.

18 Claims, 1 Drawing Sheet

FOREIGN PATENT DOCUMENTS

| WO | WO 03/103659 A1 | 12/2003 |
| --- | --- | --- |
| WO | WO 2005039542 A1 * | 5/2005 |
| WO | WO 2005/092889 A1 | 10/2005 |

OTHER PUBLICATIONS

"Amorphous Solids: Implications for Solubility and Stability," retrieved from www.Ssciinc.com/Information/RecentPublications/Applications/AmorphousSolidsImplications/tabid/142/Default.aspx, 2003, 3 pages.

"VESIcare," retrieved from www.rxlist.com/vesicare-drug.htm, 1 page.

Ahlneck et al., "The molecular basis of moisture effects on the physical and chemical stability of drugs in the solid state," (1990), International Journal of Pharmaceutics, vol. 62, pp. 87-95.

Chidavaenzi et al., "The effect of co-spray drying with polyethylene glycol 4000 on the crystallinity and physical form of lactose" (2001), International Journal of Pharmaceutics, vol. 216, pp. 43-49.

Ching-Wei Lin et al. "Effect of particle size on the available surface area of nifedipine from nifedipinepolyethylene glycol 6000 solid dispersions," (1996), International Journal of Pharmaceutics, vol. 127, pp. 261-272.

CN 2005/800094953 Chinese Communication issued May 8, 2009, related to US 2008/0039516. English Translation Included.

CN 2005800094953 Chinese Office Action issued Apr. 11, 2008, related to US 2008/0039516. English Translation Included.

Corrigan et al., "The effect of spray drying solutions of bendroflumethiazide/polyethylene glycol. On the physicochemical properties of the resultant materials." (2003), International Journal of Pharmaceutics, vol. 262, pp. 125-137.

EP 05721391.0 European Office Communication issued Jun. 22, 2009, related to US 2008/0039516.

EP 05721391.0 Supplementary European Search Report issued Nov. 10, 2008, related to US 2008/0039516.

Hedge et al. "Antimuscarinics for the treatment of overactive bladder: Current options and emerging therapies," Current Opinion in Investigation Drugs, 2004, 5(1): 40-49.

Matsunaga et al. "Effects of Compression Pressure on Physical and Chemical Stability of Tablets Containing an Anticancer Drug TAT-59," Chem. Pharm. Bull., 1994, 42(12):2582-2587.

Mealy et al. "YM-53705 (as monohydrochloride) 1(S)-Phenyl-1,2,3,4-tetrahydroisoquinoline-2-carboxylic acid 3(R)-quinuclidinyl ester monosuccinate," Drugs of the Future, 1999, 24(8): 871-874.

Office Action issued Aug. 25, 2009 in U.S. Appl. No. 10/594,127, filed Sep. 25, 2006. (US 2008/0039516).

Office Action issued Dec. 27, 2007 in U.S. Appl. No. 10/975,210, filed Oct. 27, 2004. (US 2005/0175689).

Office Action issued Jan. 16, 2009 in U.S. Appl. No. 10/594,127, filed Sep. 25, 2006. (US 2008/0039516).

Office Action issued Jul. 1, 2008, in U.S. Appl. No. 10/594,127 (Q97391). (US 2008/0039516).

Office Action issued Jun. 11, 2009 in U.S. Appl. No. 11/721,863, filed Jun. 15, 2007. (US 2008/0103171).

Office Action issued May 27, 2009 in U.S. Appl. No. 10/975,210, filed Oct. 24, 2004. (US 2008/0039516).

PCT/JP2005/005377 International Search Report issued May 17, 2005. Related to U.S. Appl. No. 10/594,127 (US Publication No. 2008/0039516).

RU 2006137565 Russian Office Action issued Mar. 24, 2008. Related to US Publication No. 2008/0039516.

International Preliminary Report on Patentability for International Application No. PCT/JP2005/023771; International Filing Date: Dec. 26, 2005.

Mexican Office Action dated Mar. 19, 2010, corresponding to U.S. Appl. No. 10/594,127 (translation included).

Japanese Office Action dated Jan. 5, 2010, corresponding to U.S. Appl. No. 10/594,127 (translation included).

Australian Office Action dated Apr. 23, 2010, corresponding to U.S. Appl. No. 10/594,127.

Indonesian Office Action dated May 18, 2010, corresponding to U.S. Appl. No. 10/594,127 (translation included).

Chinese Office Action dated Nov. 11, 2009, corresponding to U.S. Appl. No. 11/721,863 (translation included).

Japanese Office Action dated Nov. 19, 2009, corresponding to U.S. Appl. No. 11/721,863 (translation included).

U.S. Office Action of U.S. Appl. No. 10/975,210 dated Feb. 2, 2010.

Indonesian Office Action dated May 4, 2010, corresponding to U.S. Appl. No. 11/721,863 (translation included).

Australian Office Action dated Mar. 17, 2010, corresponding to U.S. Appl. No. 11/721,863.

European Search Report dated Jan. 25, 2010 for EP Application No. 05820232, 3 pages. Corresponding to U.S. Appl. No. 10/594,127.

European Search Report dated Jan. 25, 2010 for EP Application No. 09014500, 3 pages. Corresponding to U.S. Appl. No. 11/721,864.

Third Party Observations dated Jul. 27, 2010 in EP 05721391 corresponding to U.S. Appl. No. 10/594,127 with references X1 to X3.

X1 Summary of Product Characteristics for VESIcare® 5mg and 10mg tablets published on the website of the Dutch Medicines Evaluation Board dated Dec. 15, 2003, from EP 05721391.

X2 Medicines Evaluation Board dated Dec. 16, 2003, from EP 05721391.

X3 Medicines Evaluation Board dated Dec. 16, 2003, from EP 05721391.

International Preliminary Report on Patentability issued for PCT/JP2006/314250, which corresponds to U.S. Appl. No. 11/458,582, 4 pages.

International Preliminary Report on Patentability issued for PCT/JP2004/016196, which corresponds to U.S. Appl. No. 10/975,210, 6 pages.

International Search Report issued for PCT/JP2004/016196, which corresponds to U.S. Appl. No. 10/975,210, 2 pages.

International Search Report issued in PCT/JP2006/314250, which corresponds to U.S. Appl. No. 11/458,582, 2 pages.

Korean Office Action mailed on Jun. 16, 2010 for KR Patent application No. 10-2006-7019783, which correspond to U.S. Appl. No. 10/594,197, 14 pages.

Philippine Office Action mailed on Jun. 23, 2010 for PH Patent Application No. 1-2006-501883, which corresponds to U.S. Appl. No. 10/594,127, 2 pages.

Third Party Observation dated Apr. 13, 2010 in EP application No. 05721391 corresponding to U.S. Appl. No. 10/594,127 with references 01-04.

01 Yu, Lian "Amorphous pharmaceutical solids: preparation, characterization and stabilization," Advanced Drug Delivery Reviews 2001, vol. 48, pp. 27-42.

02 Hancock et al. "Characteristics and Significance of Amorphous State in Pharmaceutical Systems," Journal of Pharmaceutical Sciences, 1997, vol. 85, No. 1, 12 pages.

03 Solifenacin Succinate: Crystallization experiments, 5 pages, 2010.

04 Shalaev et al. "How does Residual Water Affect the Solid-State Degradation of Drugs in the Amorphous State?" Journal of Pharmaceutical Sciences, 1996, vol. 85, No. 11, pp. 1137-1141.

U.S. Office Action, mailed Sep. 11, 2008, for U.S. Appl. No. 10/975,210, 14 pages.

* cited by examiner

COATED FINE PARTICLES CONTAINING DRUG FOR INTRABUCCALLY FAST DISINTEGRATING DOSAGE FORMS

TECHNICAL FIELD

The present invention relates to a drug-containing coated microparticles having an average particle diameter of 350 μm or less, for quickly disintegrating preparations in the oral cavity, wherein microparticles containing a drug and polyethylene glycol which are present in a homogeneously mixed state are coated with a film comprising a water-soluble polymer, and are further coated with a film comprising:

(1) a pH-independent water-insoluble polymer accounting for 60% or more and less than 79% of the film and (2) hydroxypropylcellulose accounting for more than 21% and 40% or less of the film.

The present invention also relates to a production method for the drug-containing coated microparticles.

BACKGROUND OF THE INVENTION

As quickly disintegrating preparations in the oral cavity, quickly disintegrating tablets in the oral cavity, chewable tablets, and fine granules, granules, powders and the like which are imparted with quickly disintegrating property in the oral cavity may be exemplified. Among them, the quickly disintegrating preparations in the oral cavity is a dosage form which has been drawing attention in recent years from the viewpoint of its user-friendness, because it can be taken easily even by a patient who has a difficulty in swallowing, and it can be taken without water. However, being a dosage form which is immediately disintegrated in the oral cavity, there is still no bitterness masking technique for the quickly disintegrating tablets in the oral cavity which is considered to be sufficient for a drug having an unpleasant taste, particularly a strong bitterness.

Since quickly disintegrating preparations in the oral cavity is not accompanied by drinking of water and a remaining period of time of the drug in the oral cavity is long, control of sufficient drug dissolution at an early stage after its administration, namely strict control in comparison with conventional preparations which are taken with water, is required. In addition, since quickly disintegrating preparations in the oral cavity are positioned in many cases as a dosage form which improves the properties when the conventional tablets which are already on the market are taken, not only the instant suppression of unpleasant taste in the oral cavity, but also the ensuring of bioavailability when made into an quickly disintegrating preparations in the oral cavity, or the ensuring of bioequivalence with conventional pharmaceutical preparations, are very important in guaranteeing their qualities, so that it is also necessary to assure quick drug dissolution when the preparation is transferred from the oral cavity into gastrointestinal tracts. Thus, it is evident that the conventionally known technique of merely adding a flavor, a sweetener and the like cannot fully cope therewith, and it is extremely difficult to apply the conventionally known film coating method or the like which uses a polymer base material, which is not assumed to be applied to quickly disintegrating preparations in the oral cavity but merely has an object of suppressing unpleasant taste for only dozens of seconds after the administration, directly to the quickly disintegrating preparations in the oral cavity for the aforementioned purpose.

As a technique which is applicable to quickly disintegrating preparations in the oral cavity, International Publication WO 02/96392 discloses, regarding bitterness suppression of a drug having high water-solubility, an invention on a drug-containing microparticles to which a film coat of a combination of a water-insoluble polymer with a water-soluble polymer is applied. Ethyl cellulose, an enteric base material hydroxypropylmethylcellulose phthalate or hydroxypropylmethylcellulose succinate, or the like is used as the water-insoluble polymer of said invention. When the approximately neutral pH in the oral cavity is taken into consideration, selection of an enteric base material is not desirable, because it leads to the leaking of the bitterness. Also, since the dissolution rate described in Examples include those which are lower than 70 to 80% in 30 minutes, there is a room for further improvement when the aforementioned viewpoint of assuring bioequivalence is taken into consideration.

In addition, International Publication WO 2005/039542 discloses a drug-containing coated microparticles for quickly disintegrating tablets in the oral cavity, in which a microparticles containing a drug having an unpleasant taste is coated with a film comprising (1) a pH-independent water-insoluble polymer wherein its ratio in the film is 60% or more and less than 80% and (2) a pH-independent water-soluble substance wherein its ratio in the film is larger than 20% and 40% or less. Said invention relates to a technique on a coated microparticles suited for the suppression of unpleasant taste of a drug, which is a microparticles having an average particle size of 350 μm or less applicable to quickly disintegrating tablets in the oral cavity, that achieved sufficient dissolution suppression in the oral cavity and quick dissolution after transfer into the stomach by the combination of a water-insoluble polymer and a water-soluble substance which do not undergo influence of pH. However, there is still a room for improvement regarding suppression of unpleasant taste when a drug is used in combination with a specific additive agent.

Thus, an object of the present invention is to provide a drug-containing coated microparticles which does not undergo influence of pH, sufficiently suppresses instant unpleasant taste in the oral cavity and quickly show dissolution of the drug after transfer into gastrointestinal tracts, in the aforementioned technique of coated microparticles, even when the drug and a specified additive agent are used, for example, when solifenacin or a salt thereof and polyethylene glycol are used, as well as to provide a production method thereof.

DISCLOSURE OF THE INVENTION

It is known that certain drugs become amorphous and unstable when they are made into pharmaceutical preparations using water and the like. Accordingly, various methods are employed for the purpose of obtaining stable pharmaceutical compositions for solid use. One of the methods is to add a water-soluble substance such as polyethylene glycol or the like in the preparations with the aim of preventing solifenacin, which is known as a muscarinic receptor antagonist, from becoming amorphous.

With the aim of preventing instant unpleasant taste of solifenacin or its salt in the oral cavity and obtaining quick dissolution of a drug after transfer into gastrointestinal tracts, the present inventors have carried out various studies on microparticles which do not undergo influence of pH and can suppress unpleasant taste, and have found that it is extremely difficult to suppress unpleasant taste when solifenacin or a salt thereof and a water-soluble substance as a stabilizer for solifenacin, such as polyethylene glycol, are contained in the microparticles part. When studies were further continued on the suppression of said unpleasant taste, it was found that the aforementioned object can be achieved by coating microparticles containing a drug and polyethylene glycol with a water-soluble polymer such as hydroxypropylmethylcellulose or the like, and further applying coating of a pH-independent water-insoluble polymer and hydroxypropylcellulose, respectively in specific ratios, thus resulting in the accomplishment of the present invention. As is described later, when solifenacin or a salt thereof is selected as the drug, it is necessary that the bitterness in the oral cavity is suppressed and the bioavailability is not reduced. Accordingly, one of the objects of the present invention is to provide a drug-containing coated microparticles applicable to a quickly disintegrating preparations in the oral cavity, which sufficiently suppresses bitterness in the oral cavity and does not reduce bioavailability of solifenacin, even in the case of microparticles containing solifenacin or a salt thereof and polyethylene glycol. So far, nothing is known about the technique which solved the aforementioned problem by coating microparticles containing solifenacin or a salt thereof and polyethylene glycol with a water-soluble polymer, and a water-insoluble polymer and hydroxypropylcellulose, respectively in the specific ratios, in that order.

Accordingly, the present invention relates to:

1. A drug-containing coated microparticles having an average particle diameter of 350 μm or less, for quickly disintegrating preparations in the oral cavity, wherein microparticles containing a drug and polyethylene glycol which are present in a homogeneously mixed state are coated with a film comprising a water-soluble polymer, and are further coated with a film comprising:

(1) a pH-independent water-insoluble polymer accounting for 60% or more and less than 79% of the film and (2) hydroxypropylcellulose accounting for more than 21% and 40% or less of the film.

2. The drug-containing coated microparticles for use in a quickly disintegrating preparations in the oral cavity described in 1. above, wherein the water-soluble polymer is one or more selected from the group consisting of hydroxypropylmethylcellulose, hydroxypropylcellulose and methyl cellulose.

3. The drug-containing coated microparticles for use in a quickly disintegrating preparations in the oral cavity described in 1. or 2. above, wherein the pH-independent water-insoluble polymer is ethyl cellulose.

4. The drug-containing coated microparticles for use in a quickly disintegrating preparations in the oral cavity described in 1. to 3. above, wherein the drug is solifenacin or a salt thereof.

5. The drug-containing coated microparticles for use in a quickly disintegrating preparations in the oral cavity described in 1. to 4. above, wherein rate of dissolution of drug from the drug-containing coated microparticles using a test liquid simulating inside of the oral cavity is from 0% to 3% in 1 minute and from 0% to 25% in 3 minutes, and rate of dissolution of drug from the drug-containing coated microparticles using a test liquid simulating inside the gastrointestinal tract is 80% or more in 30 minutes.

6. A method for producing a drug-containing coated microparticles having an average particle diameter of 350 μm or less, for quickly disintegrating preparations in the oral cavity, wherein microparticles containing a drug and polyethylene glycol which are present in a homogeneously mixed state are coated with a film comprising a water-soluble polymer, and are further coated with a film comprising:

(1) a pH-independent water-insoluble polymer accounting for 60% or more and less than 79% of the film and (2) hydroxypropylcellulose accounting for more than 21% and 40% or less of the film.

7. A quickly disintegrating preparations in the oral cavity containing a drug-containing coated microparticles having an average particle diameter of 350 μm or less, for quickly disintegrating preparations in the oral cavity, wherein microparticles containing a drug and polyethylene glycol which are present in a homogeneously mixed state are coated with a film comprising a water-soluble polymer, and are further coated with a film comprising:

(1) a pH-independent water-insoluble polymer accounting for 60% or more and less than 79% of the film and (2) hydroxypropylcellulose accounting for more than 21% and 40% or less of the film.

The "homogeneously mixed state" according to the present invention means a state in which a drug and a water-soluble substance are homogeneously mixed with each other. For example, this is achieved by a method in which a drug and polyethylene glycol are dissolved, and the solution or suspension is sprayed on a spherical microparticles and dried to form a matrix of the drug and water-soluble substance on said spherical microparticles, a method in which a spherical microparticles are prepared by mixing a drug and polyethylene glycol and granulating the mixture or the like, and the like. In addition, it is also achieved by carrying out spray drying or the like using a solution containing a drug and polyethylene glycol.

The "unpleasant taste" according to the present invention means a taste which produces an unpleasant feeling at the time of taking, and illustratively indicates bitter taste, tart taste, acrid taste and the like tastes and also astringency and the like.

The polyethylene glycol to be used in the present invention is a pharmaceutically acceptable one, and its examples include polyethylene glycol 400, polyethylene glycol 600, polyethylene glycol 1000, polyethylene glycol 1500, polyethylene glycol 4000, polyethylene glycol 6000, polyethylene glycol 8000, polyethylene glycol 20000, polyethylene glycol 35000 and the like. These may be used in combination.

In addition, a water-soluble substance which shows an effect similar to that of polyethylene glycol may also be selected. Though not particularly limited to the following substances, its examples include hydroxypropylmethylcellulose, hydroxypropylcellulose, polyvinyl pyrrolidone and the like. It is possible to use them by mixing with polyethylene glycol.

Examples of the water-soluble polymer to be used in the present invention include a cellulose-based water-soluble polymer, and illustratively, hydroxypropylmethylcellulose, hydroxypropylcellulose and/or methyl cellulose. Coating with hydroxypropylmethylcellulose, hydroxypropylcellulose and/or methyl cellulose is selected as the optimum embodiment for achieving the effect of the present invention, together with the coating layer which is the outer layer of a pH-independent water-insoluble polymer and hydroxypropylcellulose. Examples of the hydroxypropylmethylcellulose which may be used in the present invention include hydroxypropylmethylcellulose 2910 (Shin-Etsu Chemical Co., Ltd.: TC-5E, TC-5R, TC-5S, metolose 60SH), hydroxypropylmethylcellulose 2906 (Shin-Etsu Chemical Co., Ltd.: metolose 65SH), hydroxypropylmethylcellulose 2208 (Shin-Etsu Chemical Co., Ltd.: metolose 90SH) and the like. In addition, examples of the hydroxypropylcellulose which may be used in the present invention include hydroxypropylcellulose (Nippon Soda Co., Ltd.: SSL type, SL type, L type, M type, H type) and the like.

The coating amount of said coated layer per the drug-containing microparticles may be optionally selected by taking the degree of bitter taste masking and drug dissolution rate into consideration and, for example, it is from 0.5 to 100% by weight based on the drug-containing microparticles containing a drug having a bitter taste which must be suppressed. The coating amount is more preferably from 1 to 50% by weight, further preferably from 1 to 25% by weight, more further preferably from 1 to 10% by weight.

The "pH-independent" means that the property of the water-insoluble polymer, that it does not dissolve in water as described below, is not changed regardless of the pH, namely even when it is acidic pH or basic pH.

The "pH-independent water-insoluble polymer" which may be used in the present invention is not particularly limited, with the proviso that it is pharmaceutically acceptable and does not dissolve in water at any pH. Its examples include cellulose-based polymers such as ethyl cellulose (e.g., Dow Chemical Co.: ETHOCEL STD10, 7P, 10P, 20P), cellulose acetate and the like, and pH-independent acryl-based polymers such as an aminoalkylmethacrylate copolymer RL (e.g., product name EUDRAGIT RL, manufactured by ROEHM), RS of the same (e.g., product name EUDRAGIT RS, manufactured by ROEHM), an ethyl acrylate methyl methacrylate copolymer (e.g., product name EUDRAGIT NE30D, manufactured by ROEHM) and the like. Particularly preferred is ethyl cellulose. It is possible to use one of the water-insoluble polymers or by optionally combining two or more.

The compositional ratio of the pH-independent water-insoluble polymer and hydroxypropylcellulose as the outer layer is selected for the purpose of achieving the object of the present invention. The ratio of the water-insoluble polymer in the coating base material is preferably 60% by weight or more and less than 79% by weight, more preferably 63% by weight or more and less than 79% by weight, further preferably 65% by weight or more and less than 78% by weight, more further preferably 68% by weight or more and less than 77% by weight, most preferably 70% by weight or more and 75% by weight or less. When the ratio of water-insoluble polymer becomes less than 60% by weight or becomes 79% by weight or more, it becomes difficult to suppress unpleasant taste in the oral cavity and achieve quick dissolution in the gastrointestinal tract. In addition to this, the case of less than 60% by weight is not suited for the practical production, because the coating amount for suppressing unpleasant taste becomes large so that prolonged production time is required.

The coating amount of the said coated layer containing the water-insoluble polymer and hydroxypropylcellulose is optionally selected by taking the degree of bitter taste masking and drug dissolution rate into consideration and therefore is not particularly limited. Since the production time is prolonged as the coating amount increases, a smaller coating amount is preferable. For example, it is from 0.5 to 200% by weight based on the drug-containing microparticles which contains a drug having bitter taste that must be suppressed. The coating amount is more preferably from 1 to 150% by weight, further preferably from 5 to 120% by weight, more further desirably from 10 to 100% by weight. When the coating amount is lower than 0.5% by weight, drug dissolution in the oral cavity may not be controlled sufficiently, thus posing a possibility of generating unpleasant taste in the oral cavity.

The aforementioned selection of water-soluble polymer, water-insoluble polymer and the like and blending ratio thereof and the like render possible suppression of unpleasant taste of a drug having markedly strong bitter taste, astringent taste and the like in the oral cavity and quick drug dissolution in the stomach, which have been difficult to achieve in applying to quickly disintegrating preparations in the oral cavity.

In this connection, when a damage is made on the coating layer of the drug-containing coated microparticles due to a tablet compression procedure in producing quickly disintegrating tablets in the oral cavity or the like using the drug-containing coated microparticles of the present invention, it is possible to cover it with an appropriate coating for the purpose of alleviating the impact by tablet compression.

The drug to be used in the present invention is not particularly limited with the proviso that it is used as a pharmaceutically active component and has an unpleasant taste.

Examples of such a drug include an antidepressant, a hypnotic sedative, a sleep inducer, an anti-anxiety agent, an anti-epileptic, an anti-migraine agent, an antipyretic-Analgesic-anti-inflammatory drug, an antiparkinsonism drug, an agent for psychoneurosis use, a drug for dementia, other agents affecting central nervous system, a muscle relaxant, an autonomic, an antispasmodic agent, a cardiotonic, an anti-arrhythmic agent, a diuretic, a hypotensive drug, a vasoconstrictor drug, a coronary vasodilator, a peripheral vasodilator, an anti-hyperlipemia agent, other circulatory agents, an anti-tussive-expectorant, a bronchodilator, other anti-allergic agents, an antidiarrheal drug, a drug for controlling intestinal function, an antiulcer drug, a stomachic-digestant, an antacid, other agents affecting gastrointestinal organs, a hormone preparation such as a pituitary hormone preparation, a thyroid hormone preparation or an anti-thyroid hormone preparation, an agent for urinary organ use, a vitamin preparation, a hemostatic, an anticoagulant, an agent for hepatic disease use, an antidote, an agent for habitual intoxication use, a drug for treatment of gout, an agent for treatment of diabetes, an agent for treatment of malignant tumor, an antihistaminic, a crude drug, kampo (a Chinese herbal medicine), an antibiotic, a chemotherapeutic agent, a vermicide, an anti-protozoan drug and the like. Illustratively, imipramine, donepezil, diphenhydramine, sumatriptan, naratriptane, eletriptan, rizatriptan, zolmitriptan, almotriptan, frovatriptan, meclo fenoxate hydrochloride, chloramphenicol, aminophylline, erythromycin, josamycin, calcium hopantenate, phenobarbital, cimetidine, famotidine, atorvastatin calcium, tamsulosin, telmisartan, tacrolimus, zolbidem, quetiapin, sulpiride, cefdiinir, micafungin, fluvoxamine, etilefrine hydrochloride, diltiazem hydrochloride, propranolol hydrochloride, flufenamic acid, digitoxin, theophylline, promethazine hydrochloride, quinine hydrochloride, sulpyrine, ibuprofen, acetaminophen, ibuprofen, celecoxib, valdecoxib, amantadine hydrochloride, oseltamivir phosphate, clarithromycin, aciclovir, norfloxacin, cefcapene pivoxil hydrochloride, ramosetron, solifenacin, solifenacin succinate, nateglinide and the like may be exemplified. These drugs may be used alone or by optionally combining two or more of them, and may be used as salts of respective drugs.

Among these examples, solifenacin or a salt thereof is particularly suitable. It is known that solifenacin or a salt thereof is orally used once a day at a dose of from 2.5 mg to 10.0 mg per day, as a therapeutic agent for frequent urination and urinary incontinence aiming at improving frequent urination, urinary incontinence, urinary urgency and the like symptoms accompanied by overactive bladder, by effecting relaxation of bladder smooth muscle through blocking of the muscarinic receptor which is present in the bladder smooth muscle (Japanese Patent No. 3014457, corresponding U.S. Pat. No. 6,017,927).

The amount of the drug contained according to the present invention is optionally selected generally depending on the kind of the drug or use of the drug (indication), but is not particularly limited with the proviso that it is a therapeutically effective amount or a prophylactically effective amount. It is preferably from 0.5 to 85% by weight, more preferably from 5 to 80% by weight, based on the whole coated microparticles. More preferable amount of the drug contained is from 10 to 70% by weight, and further more preferable the amount is from 10 to 50% by weight.

Size of the drug-containing coated microparticles for quickly disintegrating preparations in the oral cavity of the present invention is not particularly limited, with the proviso that it is a size which does not give a sand-like rough feeling when an quickly disintegrating preparations containing the microparticles is taken, but the average particle size is prepared preferably into 350 µm or less. The average particle size is more preferably from 1 to 350 µm, most preferably from 20 to 350 µm.

When a drug-containing coated microparticles is contained in quickly disintegrating preparations in the oral cavity, the coated microparticles may be included in an amount of from 0.5 to 95% by weight equivalent of the whole quickly disintegrating preparations in the oral cavity. It is preferably from 1 to 70% by weight, more preferably from 5 to 50% by weight equivalent.

The additives generally used in this field may be used in the coated microparticles of the present invention, conventionally used additives may be used alone and/or by optionally combining two or more of them. As such additives, a binder, a disintegrator, a thickener, an excipient, a lubricant, a gelling agent, a flavoring agent, an aromatic and the like may be cited. For example, as the binder, polyvinyl pyrrolidone, hydroxypropylmethylcellulose, hydroxypropylcellulose, gum arabic powder, gelatin, pullulan, polyvinyl alcohol, alpha starch and the like may be cited. Though there is a case in which they are used duplicating with the water-soluble substances of the present invention, it is possible to use them within such a range that the effect of the present invention is not spoiled. As the disintegrator, starches such as corn starch, partial alpha starch and the like, carmellose calcium, crospolyvidone, low substitution degree hydroxypropylcellulose, crystalline cellulose, croscarmellose sodium and the like may be cited. As the thickener, sodium polyacrylate, polyethylene oxide, polycarbophil, hydroxypropylmethylcellulose, hydroxypropylcellulose, sodium alginate, propylene glycol alginate, carrageenan and the like may be cited. As the excipient, lactose, corn starch, microcrystalline cellulose and the like may be cited. As the lubricant, magnesium stearate, calcium stearate, sucrose fatty acid ester, polyethylene glycol, talc, stearic acid and the like may be cited. As the gelling agent, sodium polyacrylate, polyethylene oxide, polycarbophil, hydroxypropylmethylcellulose, hydroxypropylcellulose, sodium alginate, mannan, pectin, agar, carrageenan and the like may be cited. As the flavoring agent, aspartame, sucralose, saccharin sodium, dipotassium glycyrrhizinate, stevia, thaumatin, citric acid and the like may be cited. As the aromatic, menthol, peppermint, lemon, lemon lime, orange, mentha oil and the like may be cited. These additives are examples and not limited thereto.

The drug-coated microparticles of the present invention suppresses unpleasant taste of a drug in the oral cavity and attains quick drug dissolution after its transfer into the gastrointestinal tracts. That is, for example, regarding the suppression of unpleasant taste in the oral cavity, when its dissolution is measured using a phosphate buffer of pH 6.8 (the second solution of dissolution test, The Pharmacopoeia of Japan), it is necessary that the drug dissolution rate after commencement of the dissolution test is from 0% to 10% in 1 minute, more preferably from 0% to 5% in 1 minute, further preferably from 0% to 3% in 1 minute, and from 0% to 25% in 3 minutes. This is because sufficient suppression of unpleasant taste of a drug such as solifenacin or a salt thereof in the oral cavity becomes possible when the drug dissolution is controlled at this dissolution ratio or less (Test Examples 2 and 3).

In addition, regarding the quick dissolution after transfer into the gastrointestinal tracts, when its dissolution is measured using a phosphate buffer of pH 6.8 (the second solution of dissolution test, The Pharmacopoeia of Japan) or purified water, it is necessary that the drug dissolution rate at 30 minutes after commencement of the dissolution test is 80% or more, preferably the drug dissolution ratio at 25 minutes is 80% or more, more preferably the drug dissolution ratio at 20 minutes is 80% or more, further preferably the drug dissolution ratio at 15 minutes is 80% or more. This is because said dissolution rate renders possible prevention of the reduction of bioavailability when conventional pharmaceutical preparations are administered. This value is a value obtained by the Test Example 6 shown in the following examined by the inventors.

When quickly disintegrating tablets in the oral cavity are produced by blending the drug-containing coated microparticles of the present invention with a quickly disintegrating tablets base material, the quickly disintegrating tablets may be prepared utilizing the methods described in the aforementioned references.

Illustratively, when the quickly disintegrating tablets described in International Publication 95-20380 are prepared, the drug-containing coated microparticles of the present invention is mixed with a saccharide having a low moldability and then coated and/or granulated using a saccharide having a high moldability. This granules are compressed into tablets and then humidification and drying treatment are carried out as occasion demands, thereby obtaining quickly disintegrating tablets in the oral cavity. In addition, when the quickly disintegrating tablets described in International Publication 2002-92057 are prepared, the drug-containing coated microparticles of the present invention is mixed with a diluent, and then granulated using a saccharide having a relatively low melting point from the contained drug-containing coated microparticles and said diluent. This granules are compressed into tablets and then heating treatment is carried out as occasion demands, thereby obtaining quickly disintegrating tablets in the oral cavity.

It is possible to apply to quickly disintegrating tablets in the oral cavity of other than the aforementioned ones, for example, it may be applied to those of mold type disclosed in JP-B-62-50445 or Japanese Patent No. 2807346, wet type of JP-A-5-271054 and conventional tablet compression type of JP-A-10-182436, Japanese Patent No. 3412694, International Publication WO 98/02185 or the like. It is possible to include the techniques described in these references in the present invention.

Next, production method of the drug-containing coated microparticles of the present invention is described.

Though it is possible to use the drug itself as the core in producing the drug-containing coated microparticles of the present invention, in general, drug-containing microparticles which become the drug-containing core is produced in advance. Conventionally known techniques may be applied to the production of the drug-containing microparticles to be used as the core, and for example, drug core microparticles is prepared by mixing a drug with polyethylene glycol, and this is granulated using a binder (e.g., hydroxypropylcellulose or the like), subjected to the selecting of granules and drying, or by spraying a solution or dispersion containing a drug, polyethylene glycol and, as occasion demands, a binder and/or a film forming agent to an appropriate microparticles to be used as the core (e.g. microcrystalline cellulose granules, sucrose granule, lactose granule or the like). By these methods, it becomes possible to make the drug and polyethylene glycol into a homogeneously mixed state.

The step for coating the thus prepared drug core microparticles with a water-soluble polymer has a step for preparing a coating liquid and a step for carrying out coating. The coating liquid is prepared by dissolving or dispersing a water-soluble polymer in a solvent such as water, ethanol, methanol or the like. As a matter of course, it is possible to use these solvents by optionally mixing them. The coating may be carried out by utilizing a conventionally known equipment or method, for example, by a fluidized bed granulator or the like, and the coated microparticles is prepared by spraying a liquid in which the water-soluble polymer has been dissolved.

The step for coating the aforementioned coated microparticles with an outer layer base material has a step for preparing a coating liquid and a step for carrying out coating. The coating liquid is prepared by dissolving or dispersing outer layer base material in a solvent such as water, ethanol, methanol or the like. The coating may be carried out by a fluidized bed granulator or the like, and the desired drug-containing coated microparticles in which the unpleasant taste is suppressed is obtained by optionally adjusting the amount of the coating liquid containing the outer layer base per the drug-containing coated microparticles containing a drug and a water-soluble polymer. Various kinds of upside spray type, side spray type, downside spray type and the like film coating methods may be selected, of which a side spray type method is desirable. The use of the side spray type film coating method renders possible efficient production of minutely coated drug-containing coated microparticles which are free from aggregation and have narrow particle size distribution.

Next, the production method of a quickly disintegrating tablets in the oral cavity containing the drug-containing coated microparticles of the present invention is described.

The drug-containing coated microparticles of the present invention is a suitable particle for making an quickly disintegrating tablets by blending it with a base material for quickly disintegrating tablets base material, and as such quickly disintegrating tablets which contain the drug-containing coated microparticles, the quickly disintegrating tablets described in International Publication 95-20380, JP-A-8-19589, JP-A-9-48726, Japanese Patent No. 2919771, Japanese Patent No. 3069458, International Publication 2002-92057 and the like may cited.

Saccharides are used as the base material for quickly disintegrating tablets use, and the saccharides may be optionally selected, such as general saccharides, a combination of a saccharide having a low moldability with a saccharide having a high moldability, a combination of a crystalline saccharide with an amorphous saccharide, a combination of a saccharide having a high melting point with a saccharide having a low melting point and the like. As an example thereof, a process may be employed in which the drug-containing coated microparticles of the present invention is mixed with the aforementioned saccharides having a low moldability, or the drug-containing coated microparticles of the present invention is mixed with the saccharides having a low moldability and a part of the saccharide having a high moldability, said mixture is sprayed using the saccharide having a high moldability as the binder to effect coating and/or granulation, and said granules is compression-molded.

The aforementioned saccharides having a low moldability means those which show a tablet hardness of, for example, from 0 to 2 kp when 150 mg of the saccharides are compressed into a tablet using a pestle of 8 mm in diameter under a tablet compression force of from 10 to 50 kg/cm$^2$, and the saccharides having a high moldability means those which show a hardness of 2 kp or more by the same method. The saccharides having a low moldability are those which are pharmaceutically acceptable, and lactose, mannitol, glucose, xylitol, erythritol and the like may be cited. It is possible to use them alone or by an optional combination of two or more. The saccharides having a high moldability are those which are pharmaceutically acceptable, and maltose, maltitol, sorbitol, trehalose and the like may be cited. It is also possible to use such saccharides alone or by an optional combination of two or more.

As another example, it is also possible to mix the drug-containing coated microparticles of the present invention with a diluent and a saccharide having a relatively lower melting point than that of said diluent, to spray such a mixture using a binder for quickly disintegrating tablets use to effect coating and/or granulation, and then to carry out compression molding of said granulated material. As said techniques, the techniques described in International Publication WO 02/092057 may be employed, and the aforementioned and following "saccharides having a high melting point" and "saccharides having a low melting point" are those which come under the definition described in said reference, and the substances shown in the following may be used.

The aforementioned saccharides having a high melting point are pharmaceutically acceptable materials, which are selected from the saccharides having a relatively higher melting point than that of the saccharides having a low melting point. For example, xylitol, trehalose, maltose, sorbitol, erythritol, glucose, sucrose, maltitol, mannitol and the like may be cited. It is possible to use them alone or by optionally combining two or more of them. The saccharides having a low melting point are pharmaceutically acceptable materials, and for example, xylitol, trehalose, maltose, sorbitol, erythritol, glucose, sucrose, maltitol, mannitol and the like may be cited. It is also possible to use them alone or by optionally combining two or more of them. There are duplications between the saccharides having a high moldability and saccharides having a low moldability, because they are selected based on whether their melting points are relatively high or low. As the binder for quickly disintegrating tablets use, maltitol, copolyvidone and the like may be exemplified. It is also possible to use such binders alone or by optionally combining two or more of them.

In order to further increase hardness of the thus prepared moldings, steps for humidification and drying treatment may be employed. The "humidification" is determined by the apparent critical relative humidity of the saccharides to be contained, and the humidification is generally carried out at the critical relative humidity or more. For example, it is from 30 to 100% RH, preferably from 50 to 90% RH, as humidity. The temperature in this case is preferably from 15 to 50° C., more preferably from 20 to 40° C. The treating time is from 1 to 36 hours, preferably from 12 to 24 hours. The "drying" is not particularly limited with the proviso that it is a step for removing the moisture absorbed by the humidification. For example, from 10 to 100° C. may be set, and preferably from 20 to 60° C., more preferably from 25 to 40° C. may be set, as the temperature condition of the drying. The treating time may be set to 0.5 to 5 hours, preferably from 1 to 3 hours.

When saccharides having a high and a low melting points are used in combination, a heating step may also be employed for the purpose of increasing hardness of the prepared moldings. The "heating" is determined by the melting point of the contained saccharide having a low melting point, and the heating is carried out generally at a temperature of the lower side melting point or more and less than the higher side melting point. The treating time may be set to from 0.5 to 120 minutes, preferably from 1 to 60 minutes.

THE BEST MODE FOR CARRYING OUT THE INVENTION

Figure 1:
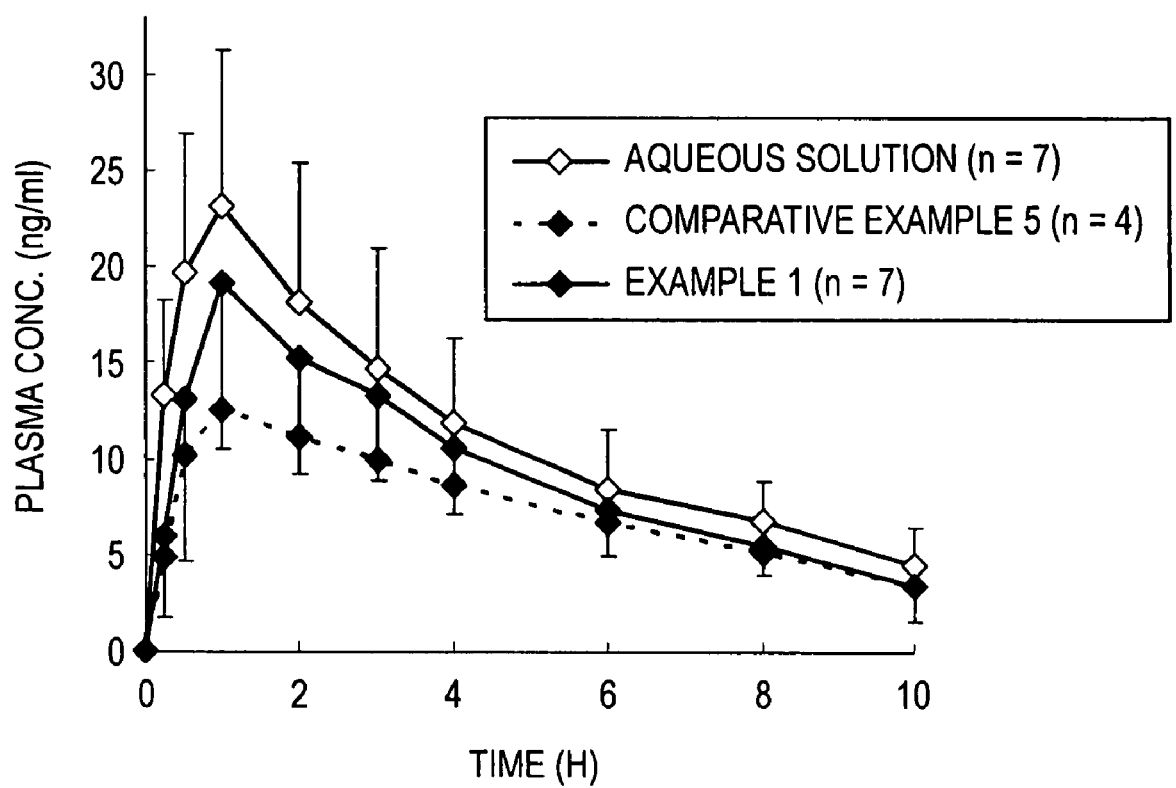
FIG. 1 shows changes in the blood concentration of solifenacin succinate when solifenacin succinate-containing coated microparticles is orally administered to a beagle.

The following illustratively describes the present invention with reference to Examples, but the scope of the invention should not be interpreted limitedly thereby.

Example 1

Preparation of a Drug-Containing Coated Microparticles for an Quickly Disintegrating Tablets in the Oral Cavity in which Unpleasant Taste is Suppressed (Coat Film Composition: Ethyl Cellulose/Hydroxypropylcellulose=75/25 Coating)

[Preparation of a Drug-Containing Microparticles]

(Solifenacin-Polyethylene Glycol-Celphere)

A 600.0 g portion of spherical granules made of crystalline cellulose (manufactured by ASAHI CHEMICAL INDUSTRY CO., LTD.; Celphere CP-102Y) was weighed, and a mixed liquid of 798.0 g of water and 798.0 g of methanol in which 300.0 g of solifenacin succinate and 102.0 g of polyethylene glycol 6000 (manufactured by Sanyo Kasei; Macrogol 6000, corresponds to polyethylene glycol 8000 and Macrogol 8000, respectively in USP and EP) were dissolved was sprayed thereto using a fluidized bed granulator (manufactured by Glatt, GPCG-1) at a setting temperature of 57° C., a product temperature of 41° C. and a spray rate of 9.0 g/min and under a spray air pressure of 2.5 kgf/cm$^2$, thereby obtaining solifenacin succinate drug-containing microparticles. The coating amount of solifenacin succinate was set to 50% based on the core microparticles Celphere CP-102Y.

[Preparation of Coating Liquid of Hydroxypropylmethylcellulose]

A coating solution of a water-soluble polymer hydroxypropylmethylcellulose was prepared. A 22.5 g portion of Hydroxypropylmethylcellulose 2910 (manufactured by Shin-Etsu Chemical Co., Ltd.: TC-5R) was dissolved in a mixed liquid of 214.0 g of water and 214.0 g of methanol and used as the coating solution.

[Practice of Coating of Hydroxypropylmethylcellulose]

A 450.0 g portion of the aforementioned solifenacin succinate drug microparticles were coated with the aforementioned coating solution using a fluidized bed granulator (manufactured by Glatt, GPCG-1). The production conditions were setting temperature 56° C., product temperature 38° C., spray rate 5.9 g/min and spray air pressure 2.0 kgf/cm$^2$, and the coated amount calculated from the weight of the solifenacin succinate drug microparticles and the weight of solid components of the coated coating liquid was set to 5% based on the solifenacin succinate drug microparticles.

[Preparation of Outer Layer Coating Liquid]

A coating solution having a compositional ratio of a water-insoluble polymer ethyl cellulose and a water-soluble polymer hydroxypropylcellulose of 75/25 was prepared. A 90.0 g portion of ethyl cellulose (Dow Chemical Co.; ETHOCEL STD10) and 30.0 g of hydroxypropylcellulose (manufactured by Nippon Soda Co., Ltd.; HPC-SL) were homogeneously dissolved in 2280.0 g of methanol and used as the coating solution.

[Practice of Outer Layer Coating]

A 420.0 g portion of the aforementioned hydroxypropylmethylcellulose-coated microparticles were coated with the aforementioned outer layer coating solution using a fluidized bed granulator (manufactured by Glatt, GPCG-1), thereby obtaining outer layer-coated microparticles to which taste-masking treatment was applied. The production conditions were setting temperature 48° C., product temperature 38° C., spray rate 5.5 g/min and spray air pressure 2.0 kgf/cm$^2$, and the coated amount calculated from the weight of hydroxypropylmethylcellulose-coated microparticles and the weight of solid components of the coated coating liquid was set to 30% based on the solifenacin succinate drug microparticles. In this case, average particle size of the outer layer-coated microparticles was 180 µm.

Example 2

Preparation of a Drug-Containing Coated Microparticles for an Quickly Disintegrating Tablets in the Oral Cavity in which Unpleasant Taste is Suppressed (Coat Film Composition: Ethyl Cellulose/Hydroxypropylcellulose=75/25 coating, the drug content is different from Example 1)

[Preparation of a Drug Microparticles]

A 600.0 g portion of spherical granules made of crystalline cellulose (manufactured by ASAHI CHEMICAL INDUSTRY CO., LTD.; Celphere CP-102Y) was weighed, and a mixed liquid of 266.0 g of water and 266.0 g of methanol in which 100.0 g of solifenacin succinate and 34.0 g of polyethylene glycol 6000 (manufactured by Sanyo Kasei; Macrogol 6000, corresponds to polyethylene glycol 8000 and Macrogol 8000, respectively in USP and EP) were dissolved was sprayed thereto using a fluidized bed granulator (manufactured by Glatt, GPCG-1) at a setting temperature of 60° C., a product temperature of 46° C. and a spray rate of 7.8 g/min and under a spray air pressure of 3.0 kgf/cm$^2$, thereby obtaining solifenacin succinate drug-containing microparticles. Coating amount of solifenacin succinate was set to about 17% based on the core microparticles Celphere CP-102Y.

[Preparation of Coating Liquid of Hydroxypropylmethylcellulose]

A coating solution of a water-soluble polymer hydroxypropylmethylcellulose was prepared. A 20.0 g portion of Hydroxypropylmethylcellulose 2910 (manufactured by Shin-Etsu Chemical Co., Ltd.: TC-5R) was dissolved in a mixed liquid of 190.0 g of water and 190.0 g of methanol and used as the coating solution.

[Practice of Coating of Hydroxypropylmethylcellulose]

A 400.0 g portion of the aforementioned solifenacin succinate drug-containing microparticles were coated with the aforementioned coating solution using a fluidized bed granulator (manufactured by Glatt, GPCG-1). The production conditions were setting temperature 55° C., product temperature 38° C., spray rate 5.2 g/min and spray air pressure 2.0 kgf/cm$^2$, and the coated amount calculated from the weight of the solifenacin succinate drug microparticles and the weight of solid components of the coated coating liquid was set to 5% based on the solifenacin succinate drug-containing microparticles.

[Preparation of Outer Layer Coating Liquid]

A coating solution having a compositional ratio of a water-insoluble polymer ethyl cellulose and a water-soluble polymer hydroxypropylcellulose of 75/25 was prepared. A 120.0 g portion of ethyl cellulose and 40.0 g of hydroxypropylcellulose (manufactured by Nippon Soda Co., Ltd.; HPC-SL) were homogeneously dissolved in 3040.0 g of methanol and used as the coating solution.

[Practice of Outer Layer Coating]

A 420.0 g portion of the aforementioned hydroxypropylmethylcellulose-coated microparticles were coated with the aforementioned outer layer coating solution using a fluidized bed granulator (manufactured by Glatt, GPCG-1), thereby obtaining outer layer-coated microparticles to which taste-masking treatment was applied. The production conditions were setting temperature 50° C., product temperature 38° C., spray rate 5.6 g/min and spray air pressure 2.0 kgf/cm$^2$, and the coated amount calculated from the weight of the hydroxypropylmethylcellulose-coated microparticles and the weight of solid components of the coated coating liquid was set to 40% based on the solifenacin succinate drug-containing microparticles. In this case, average particle size of the outer layer-coated microparticles was 166 µm.

Example 3

Preparation of a Drug-Containing Coated Microparticles for an Quickly Disintegrating Tablets in the Oral Cavity in which Unpleasant Taste is Suppressed (Coat Film Composition: Ethyl Cellulose/Hydroxypropylcellulose=75/25 Coating, the Drug Content and the Spherical Granule used as the Core are Different from Example 1)

[Preparation of a Drug Microparticles]

A 245.0 g portion of spherical granules made of crystalline cellulose (manufactured by ASAHI CHEMICAL INDUSTRY CO., LTD.; Celphere SCP-100) was weighed, and a mixed liquid of 1137.0 g of water and 1137.0 g of methanol in which 350.0 g of solifenacin succinate and 105.0 g of polyethylene glycol 6000 (manufactured by Sanyo Kasei; Macrogol 6000, corresponds to polyethylene glycol 8000 and Macrogol 8000, respectively in USP and EP) were dissolved was sprayed thereto using a fluidized bed granulator (manufactured by Freund Corporation; UNI-GLATT) at a setting temperature of 95° C., a product temperature of 36° C. and a spray rate of 12.0 g/min and under a spray air pressure of 3.0 kgf/cm$^2$, thereby obtaining solifenacin succinate drug-containing microparticles. Coating amount of solifenacin succinate was set to 143% based on the core microparticles Celphere SCP-100.

[Preparation of Coating Liquid of Hydroxypropylmethylcellulose]

A coating solution of a water-soluble polymer hydroxypropylmethylcellulose was prepared. A 15.0 g portion of Hydroxypropylmethylcellulose 2910 (manufactured by Shin-Etsu Chemical Co., Ltd.: TC-5R) was dissolved in a mixed liquid of 142.5 q of water and 142.5 g of methanol and used as the coating solution.

[Practice of Coating of Hydroxypropylmethylcellulose]

A 300.0 g portion of the aforementioned solifenacin succinate drug microparticles were coated with the aforementioned coating solution using a fluidized bed granulator (manufactured by Freund Corporation; UNI-GLATT). The production conditions were setting temperature 70° C., product temperature 38° C., spray rate 6.0 g/min and spray air pressure 3.0 kgf/cm$^2$, and the coated amount calculated from the weight of the solifenacin succinate drug microparticles and the weight of solid components of the coated coating liquid was set to 5% based on the solifenacin succinate drug-containing microparticles.

[Preparation of Outer Layer Coating Liquid]

A coating solution having a compositional ratio of a water-insoluble polymer ethyl cellulose and a water-soluble polymer hydroxypropylcellulose of 75/25 was prepared. A 126.0 g portion of ethyl cellulose and 42.0 g of hydroxypropylcellulose (manufactured by Nippon Soda Co., Ltd.; HPC-SL) were homogeneously dissolved in 3192.0 g of methanol and used as the coating solution.

[Practice of Outer Layer Coating]

A 294.0 g portion of the aforementioned hydroxypropylmethylcellulose-coated microparticles were coated with the aforementioned outer layer coating solution using a fluidized bed granulator (manufactured by Freund Corporation; UNI-GLATT), thereby obtaining outer layer-coated microparticles to which taste-masking treatment was applied. The production conditions were setting temperature 70° C., product temperature 41° C., spray rate 5.9 g/min and spray air pressure 2.2 kgf/cm$^2$, and the coated amount calculated from the weight of the hydroxypropylmethylcellulose-coated microparticles and the weight of solid components of the coated coating liquid was set to 60% based on the solifenacin succinate drug-containing microparticles. In this case, average particle size of the outer layer-coated microparticles was 193 µm.

Example 4

Preparation of a Drug-Containing Coated Microparticles for an Quickly Disintegrating Tablets in the Oral Cavity in which Unpleasant Taste is Suppressed (Coat Film Composition: Ethyl Cellulose/Hydroxypropylcellulose=75/25 Coating, Grade of the Hydroxypropylcellulose Used in the Coating is Different from Example 2)

A coating solution having a compositional ratio of a water-insoluble polymer ethyl cellulose and a water-soluble polymer hydroxypropylcellulose of 75/25 was prepared. A 150.0 g portion of ethyl cellulose and 50.0 g of hydroxypropylcellulose (manufactured by Nippon Soda Co., Ltd.; HPC-SSL) were homogeneously dissolved in 3800.0 g of methanol and used as the coating solution. Solifenacin succinate drug-containing microparticles and hydroxypropylmethylcellulose-coated microparticles were prepared in accordance with the method of Example 2, and 420.0 g of the hydroxypropylmethylcellulose-coated microparticles were coated with the coating solution using a fluidized bed granulator (manufactured by Glatt, GPCG-1), thereby obtaining outer layer-coated microparticles to which taste-masking treatment was applied. The production conditions were setting temperature 50° C., product temperature 38° C., spray rate 5.3 g/min and spray air pressure 2.0 kgf/cm$^2$, and the coated amount calculated from the weight of the hydroxypropylmethylcellulose-coated microparticles and the weight of solid components of the coated coating liquid was set to 50% based on the solifenacin succinate drug microparticles. In this case, average particle size of the outer layer-coated microparticles was 173 μm.

Example 5

Preparation of a Drug-Containing Coated Microparticles for an Quickly Disintegrating Tablets in the Oral Cavity in which Unpleasant Taste is Suppressed (Coat Film Composition: Ethyl Cellulose/Hydroxypropylcellulose=75/25 Coating, Grade of the Hydroxypropylcellulose Used in the Coating is Different from Example 2)

A coating solution having a compositional ratio of a water-insoluble polymer ethyl cellulose and a water-soluble polymer hydroxypropylcellulose of 75/25 was prepared. A 120.0 g portion of ethyl cellulose and 40.0 g of hydroxypropylcellulose (manufactured by Nippon Soda Co., Ltd.; HPC-L) were homogeneously dissolved in 3040.0 g of methanol and used as the coating solution. Solifenacin succinate drug-containing microparticles and hydroxypropylmethylcellulose-coated microparticles were prepared in accordance with the method of Example 2, and 420.0 g of the hydroxypropylmethylcellulose-coated microparticles were coated with the coating solution using a fluidized bed granulator (manufactured by Glatt, GPCG-1), thereby obtaining outer layer-coated microparticles to which taste-masking treatment was applied. The production conditions were setting temperature 55° C., product temperature 41° C., spray rate 5.5 g/min and spray air pressure 2.0 kgf/cm$^2$, and the coated amount calculated from the weight of the hydroxypropylmethylcellulose-coated microparticles and the weight of solid components in the coated coating liquid was set to 40% based on the solifenacin succinate drug-containing microparticles. In this case, average particle size of the outer layer-coated microparticles was 164 μm.

Example 6

Preparation of a Drug-Containing Coated Microparticles for a Quickly Disintegrating Tablets in the Oral Cavity in which Unpleasant Taste is Suppressed (Coat Film Composition: Ethyl Cellulose/Hydroxypropylcellulose=70/30 Coating, Compositional Ratio of Ethyl Cellulose/Hydroxypropylcellulose Used in the Coating is Different from Example 2)

A coating solution having a compositional ratio of a water-insoluble polymer ethyl cellulose and a water-soluble polymer hydroxypropylcellulose of 70/30 was prepared. A 140.0 g portion of ethyl cellulose and 60.0 g of hydroxypropylcellulose (manufactured by Nippon Soda Co., Ltd.; HPC-SL) were homogeneously dissolved in 3800.0 g of methanol and used as the coating solution. Solifenacin succinate drug-containing microparticles and hydroxypropylmethylcellulose-coated microparticles were prepared in accordance with the method of Example 2, and 420.0 g of the hydroxypropylmethylcellulose-coated microparticles were coated with the coating solution using a fluidized bed granulator (manufactured by Glatt, GPCG-1), thereby obtaining outer layer-coated microparticles to which taste-masking treatment was applied. The production conditions were setting temperature 50° C., product temperature 40° C., spray rate 5.6 g/min and spray air pressure 2.0 kgf/cm$^2$, and the coated amount calculated from the weight of the hydroxypropylmethylcellulose-coated microparticles and the weight of solid components in the coated coating liquid was set to 50% based on the solifenacin succinate drug-containing microparticles. In this case, average particle size of the outer layer-coated microparticles was 165 μm.

Example 7

Preparation of Quickly Disintegrating Tablets in the Oral Cavity Containing Drug-Containing Coated Microparticles (Quickly Disintegrating Tablets Using the Coated Microparticles of Example 1)

A mixture of 740.8 g of mannitol (manufactured by Towa Chemical Industry Co., Ltd; Mannitol P) which had been pulverized with a pin mill (manufactured by Hosokawa Micron Corporation; Fine Impact Mill 100UPZ) and screened through 24 Mesh and 154.2 g of the drug-containing coated microparticles obtained in Example 1 (30% coating) was granulated with an aqueous solution containing 100.0 g of maltose (manufactured by Hayashibara; Sunmalto S) using a fluidized bed granulator (manufactured by Glatt, GPCG-1), thereby obtaining granules for quickly disintegrating tablets use.

A 960.0 g portion of the aforementioned granules was blended with 4.8 g of magnesium stearate (manufactured by Merck) and made into tablets with a weight of 300.0 mg and under a compression force of 2.0 kN, using a rotary tabletting machine (Hata Iron Works, X-20) and employing a punch and die of 9.5 mm in diameter. The tablets were preserved under heating and humidification of 25° C./70% RH for 18 hr using a thermo-hygrostat (manufactured by Tabai Espec, PR-35C), and then dried at 30° C. (humidity 40% RH) for 3 hr to obtain quickly disintegrating tablets in the oral cavity. Hardness of the obtained tablets was 4.2 kp (n=5).

Example 8

Preparation of Quickly Disintegrating Tablets in the Oral Cavity Containing Drug-Containing Coated Microparticles (Quickly Disintegrating Tablets Using the Coated Microparticles of Example 3)

[Preparation of Granulated Particles for Quickly Disintegrating Tablets Use]

Granulated particles for quickly disintegrating tablets use were obtained by granulating 1000.0 g of mannitol (manufactured by Towa Chemical Industry Co., Ltd; Mannitol P) using an aqueous solution prepared by dissolving 100.0 g of maltose in 400.0 g of water.

[Preparation of Quickly Disintegrating Tablets]

A mixture of 213.0 mg of the aforementioned granulated particles and 32.0 mg of the drug-containing coated microparticles obtained in Example 3 (55% coating) (55% coated product) was put into a die of 9.0 mm in diameter, and then made into a tablet using a single tabletting machine (Shimadzu Corp., Autograph AGS-20KGS) and under a compression force of 2.0 kN, thereby obtaining a quickly disintegrating tablets in the oral cavity.

Comparative Example 1

Preparation of Drug-Containing Coated Microparticles for Quickly Disintegrating Tablets Use, not Coated with Hydroxypropylmethylcellulose and/or Hydroxypropylcellulose (Different from Example 2 from a Viewpoint that a Water-Soluble Polymer (Hydroxypropylmethylcellulose) is not Coated and a Point that Ethyl Cellulose/Hydroxypropylmethylcellulose are Coated)

[Preparation of Outer Layer Coating Liquid]

A coating solution having a compositional ratio of a water-insoluble polymer ethyl cellulose and a water-soluble polymer hydroxypropylmethylcellulose of 75/25 was prepared. A 30.0 g portion of Hydroxypropylmethylcellulose 2910 (manufactured by Shin-Etsu Chemical Co., Ltd.; TC-5E) was homogeneously dissolved in 91.2 g of water. A 2188.8 g portion of methanol was added thereto and mixed, and then 90.0 g of ethyl cellulose was added thereto and homogeneously dissolved to be used as the coating solution.

[Practice of Outer Layer Coating]

A 400.0 g portion of the solifenacin succinate drug-containing microparticles produced in Example 2 were coated with the aforementioned coating solution using a fluidized bed granulator (manufactured by Glatt, GPCG-1), thereby obtaining outer layer-coated microparticles. The production conditions were setting temperature 51° C., product temperature 36° C., spray rate 5.8 g/min and spray air pressure 2.0 kgf/cm², and the coated amount calculated from the weight of the solifenacin succinate drug microparticles and the weight of solid components in the coated coating liquid was set to 30% based on the solifenacin succinate drug-containing microparticles. In this case, average particle size of the outer layer-coated microparticles was 161 µm.

Comparative Example 2

Preparation of Drug-Containing Coated Microparticles for Quickly Disintegrating Tablets Use, not Coated with Hydroxypropylmethylcellulose and/or Hydroxypropylcellulose (Different from Comparative Example 1 from a Viewpoint that Polyethylene Glycol is not Contained in the Drug Microparticles)

[Preparation of Drug Microparticles]

A 600.0 g portion of spherical granules made of crystalline cellulose (manufactured by ASAHI CHEMICAL INDUSTRY CO., LTD.; Celphere CP-102Y) was weighed, and a mixed liquid of 266.0 g of water and 266.0 g of methanol in which 100.0 g of solifenacin succinate and 34.0 g of Hydroxypropylmethylcellulose 2910 (manufactured by Shin-Etsu Chemical Co., Ltd.; TC-5E) were dissolved was sprayed thereto using a fluidized bed granulator (manufactured by Glatt, GPCG-1) at a setting temperature of 60° C., a product temperature of 41° C. and a spray rate of 10.0 g/min and under a spray air pressure of 3.0 kgf/cm², thereby obtaining solifenacin succinate drug-containing microparticles.

[Preparation of Outer Layer Coating Liquid]

A coating solution having a compositional ratio of a water-insoluble polymer ethyl cellulose and a water-soluble polymer hydroxypropylmethylcellulose of 75/25 was prepared. A 20.0 g portion of Hydroxypropylmethylcellulose 2910 (manufactured by Shin-Etsu Chemical Co., Ltd.; TC-5E) was homogeneously dissolved in 60.0 g of water. A 1460.0 g portion of methanol was added thereto and mixed, and then 60.0 g of ethyl cellulose was added thereto and homogeneously dissolved to be used as the coating solution.

[Practice of Outer Layer Coating]

A 400.0 g portion of the aforementioned drug-containing microparticles were coated with the aforementioned coating solution using a fluidized bed granulator (manufactured by Glatt, GPCG-1), thereby obtaining outer layer-coated microparticles. The production conditions were setting temperature 50° C., product temperature 37° C., spray rate 5.5 g/min and spray air pressure 2.0 kgf/cm², and the coated amount calculated from the weight of the solifenacin succinate drug microparticles and the weight of solid components in the coated coating liquid was set to 20% based on the solifenacin succinate drug-containing microparticles. In this case, average particle size of the outer layer-coated microparticles was 153 µm.

Comparative Example 3

Preparation of Drug-Containing Coated Microparticles for Quickly Disintegrating Tablets Use, not Coated with Hydroxypropylmethylcellulose and/or Hydroxypropylcellulose (Different from Comparative Example 1 from a Viewpoint that Polyethylene Glycol is not Contained in the Drug Microparticles)

[Preparation of Drug Microparticles]

A 600.0 g portion of spherical granules made of crystalline cellulose (manufactured by ASAHI CHEMICAL INDUSTRY CO., LTD.; Celphere CP-102Y) was weighed, and a mixed liquid of 266.0 g of water and 266.0 g of methanol in which 100.0 g of solifenacin succinate and 34.0 g of hydroxypropylcellulose (manufactured by Nippon Soda Co., Ltd.; HPC-SL) were dissolved was sprayed thereto using a fluidized bed granulator (manufactured by Glatt, GPCG-1) at a setting temperature of 55° C., a product temperature of 44° C. and a spray rate of 4.0 g/min and under a spray air pressure of 3.0 kgf/cm², thereby obtaining solifenacin succinate drug-containing microparticles.

[Preparation of Outer Layer Coating Liquid]

A coating solution having a compositional ratio of a water-insoluble polymer ethyl cellulose and a water-soluble polymer hydroxypropylmethylcellulose of 75/25 was prepared. A 22.5 g portion of Hydroxypropylmethylcellulose 2910 (manufactured by Shin-Etsu Chemical Co., Ltd.; TC-5E) was homogeneously dissolved in 67.5 g of water. A 1642.5 g portion of methanol was added thereto and mixed, and then 67.5 g of ethyl cellulose was added thereto and homogeneously dissolved to be used as the coating solution.

[Practice of Outer Layer Coating]

A 300.0 g portion of the aforementioned drug-containing microparticles were coated with the aforementioned coating solution using a fluidized bed granulator (manufactured by Glatt, GPCG-1), thereby obtaining outer layer-coated microparticles. The production conditions were setting temperature 52° C., product temperature 35° C., spray rate 5.6 g/min and spray air pressure 2.0 kgf/cm², and the coated amount calculated from the weight of the solifenacin succinate drug-containing microparticles and the weight of solid components in the coated coating liquid was set to 30% based on the solifenacin succinate drug microparticles. In this case, average particle size of the outer layer-coated microparticles was 158 μm.

Comparative Example 4

Preparation of Drug-Containing Coated Microparticles for Quickly Disintegrating Tablets Use (Coat Film Composition: Ethyl Cellulose/Hydroxypropylmethylcellulose=75/25 Coating, Different from Example 2 from a Viewpoint that Ethyl Cellulose/Hydroxypropylmethylcellulose are Coated)

[Preparation of Outer Layer Coating Liquid]

A coating solution having a compositional ratio of a water-insoluble polymer ethyl cellulose and a water-soluble polymer hydroxypropylmethylcellulose 2910 (manufactured by Shin-Etsu Chemical Co., Ltd.; TC-5E) of 75/25 was prepared. A 20.0 g portion of Hydroxypropylmethylcellulose 2910 (manufactured by Shin-Etsu Chemical Co., Ltd.; TC-5E) was homogeneously dissolved in 60.0 g of water. A 1460.0 g portion of methanol was added thereto and mixed, and then 60.0 g of ethyl cellulose was added thereto and homogeneously dissolved to be used as the coating solution.

[Practice of Outer Layer Coating]

Solifenacin succinate drug-containing microparticles and hydroxypropylmethylcellulose-coated microparticles were prepared in accordance with the method of Example 2, and 420.0 g of the thus obtained hydroxypropylmethylcellulose-coated microparticles were coated with the coating solution using a fluidized bed granulator (manufactured by Glatt, GPCG-1), thereby obtaining outer layer-coated microparticles. The production conditions were setting temperature 46° C., product temperature 37° C., spray rate 5.6 g/min and spray air pressure 2.0 kgf/cm², and the coated amount calculated from the weight of the hydroxypropylmethylcellulose-coated microparticles and the weight of solid components in the coated coating liquid was set to 20% based on the solifenacin succinate drug-containing microparticles. In this case, average particle size of the outer layer-coated microparticles was 161 μm.

Comparative Example 5

Preparation of Drug-Containing Coated Microparticles for Quickly Disintegrating Tablets Use (Coat Film Composition: Ethyl cellulose/Hydroxypropylmethylcellulose=75/25 Coating, Different from Example 1 from a Viewpoint that Ethyl Cellulose/Hydroxypropylmethylcellulose are Coated)

[Preparation of Coating Liquid of Hydroxypropylmethylcellulose]

A coating solution of a water-soluble polymer hydroxypropylmethylcellulose was prepared. A 24.0 g portion of Hydroxypropylmethylcellulose 2910 (manufactured by Shin-Etsu Chemical Co., Ltd.; TC-5R) was homogeneously dissolved in a mixed liquid of 228.0 g of water and 228.0 g of methanol and used as the coating solution.

[Practice of Coating of hydroxypropylmethylcellulose]

A 480.0 g portion of the solifenacin succinate drug-containing microparticles prepared in accordance with the method of Example 1 were coated with the aforementioned coating solution of hydroxypropylmethylcellulose using a fluidized bed granulator (manufactured by Freund Corporation, UNI-GLATT). The production conditions were setting temperature 49° C., product temperature 34° C., spray rate 5.7 g/min and spray air pressure 2.0 kgf/cm², and the coated amount calculated from the weight of the solifenacin succinate drug-containing microparticles and the weight of solid components in the coated coating liquid was set to 5% based on the solifenacin succinate drug-containing microparticles.

[Preparation of Outer Layer Coating Liquid]

A coating solution having a compositional ratio of a water-insoluble polymer ethyl cellulose and a water-soluble polymer hydroxypropylmethylcellulose of 75/25 was prepared. A 20.0 g portion of Hydroxypropylmethylcellulose 2910 (manufactured by Shin-Etsu Chemical Co., Ltd.; TC-5E) was homogeneously dissolved in 60.0 g of water. A 1460.0 g portion of methanol was added thereto and mixed, and then 60.0 g of ethyl cellulose was added thereto and homogeneously dissolved to be used as the coating solution.

[Practice of Outer Layer Coating]

A 420.0 g portion of the aforementioned hydroxypropylmethylcellulose-coated microparticles were coated with the aforementioned coating solution using a fluidized bed granulator (manufactured by Glatt, GPCG-1), thereby obtaining outer layer-coated microparticles. The production conditions were setting temperature 48° C., product temperature 40° C., spray rate 5.2 g/min and spray air pressure 2.0 kgf/cm², and the coated amount calculated from the weight of hydroxypropylmethylcellulose-coated microparticles and the weight of solid components in the coated coating liquid was set to 17% based on the solifenacin succinate drug-containing microparticles. In this case, average particle size of the outer layer-coated microparticles was 166 μm.

Comparative Example 6

Preparation of Drug-Containing Coated Microparticles for Quickly Disintegrating Tablets Use, which are not Coated with Hydroxypropylmethylcellulose and/or Hydroxypropylcellulose (Different from Example 2 from a Viewpoint that a Water-Soluble Polymer (Hydroxypropylmethylcellulose) are not Coated)

A coating solution having a compositional ratio of a water-insoluble polymer ethyl cellulose and a water-soluble polymer hydroxypropylcellulose of 75/25 was prepared. An 81.0 g portion of ethyl cellulose (Dow Chemical Co.; ETHOCEL STD 10) and 27.0 g of hydroxypropylcellulose (manufactured by Nippon Soda Co., Ltd.; HPC-SL) were homogeneously dissolved in 2052.0 g of methanol and used as the coating solution. A 360.0 g portion of solifenacin succinate drug-containing microparticles produced in accordance with the method of Example 2 were coated with the aforementioned outer layer coating solution using a fluidized bed granulator (manufactured by Glatt, GPCG-1), thereby obtaining outer layer-coated microparticles. The production conditions were setting temperature 50° C., product temperature 32° C., spray rate 6.0 g/min and spray air pressure 2.0 kgf/cm², and the coated amount calculated from the weight of the solifenacin succinate drug-containing microparticles and the weight of solid components in the coated coating liquid was set to 30% based on the solifenacin succinate drug-containing microparticles. In this case, average particle size of the outer layer-coated microparticles was 162 µm.

Comparative Example 7

Preparation of Drug-Containing Coated Microparticles for Quickly Disintegrating Tablets Use (Coat Film Composition: Ethyl Cellulose/Hydroxypropylcellulose=79/21 Coating, Different from Example 2 from a Viewpoint that Compositional Ratio of Ethyl Cellulose/Hydroxypropylcellulose Used in the Coating is Different)

A coating solution having a compositional ratio of a water-insoluble polymer ethyl cellulose and a water-soluble polymer hydroxypropylcellulose of 79/21 was prepared. A 94.8 g portion of ethyl cellulose and 25.2 g of hydroxypropylcellulose (HPC-SL) were homogeneously dissolved in 2280.0 g methanol and used as the coating solution. Solifenacin succinate drug-containing microparticles and hydroxypropylmethylcellulose-coated microparticles were prepared in accordance with the method of Example 2, and 420.0 g of the thus obtained hydroxypropylmethylcellulose-coated microparticles were coated with the coating solution using a fluidized bed granulator (manufactured by Glatt, GPCG-1), thereby obtaining outer layer-coated microparticles. The production conditions were setting temperature 50° C., product temperature 41° C., spray rate 5.5 g/min and spray air pressure 2.0 kgf/cm$^2$, and the coated amount calculated from the weight of the hydroxypropylmethylcellulose-coated microparticles and the weight of solid components in the coated coating liquid was set to 30% based on the solifenacin succinate drug-containing microparticles. In this case, average particle size of the outer layer-coated microparticles was 163 µm.

Test Example 1

Dissolution Test of Drug-Containing Coated Microparticles

The drug-containing coated microparticles obtained in Comparative Example 1, Comparative Example 2 and Comparative Example 3 were respectively weighed in such a manner that the amount as solifenacin succinate became 5 mg, and the dissolution test was carried out in accordance with the second method of the dissolution test method of The Pharmacopoeia of Japan using a six-consecutive automatic dissolution tester (manufactured by Toyama Sangyo). As the test liquid, 900 ml of pH 6.8 phosphate buffer (the second liquid of the disintegration test method of The Pharmacopoeia of Japan) was used. This was carried out at a number of paddle rotation of 50 rotations/minute (Table 1).

TABLE 1

Dissolution test results of Comparative Example 1, Comparative Example 2 and Comparative Example 3

| Outer layer coating ratio | 1 minute | 3 minutes | 30 minutes |
|---|---|---|---|
| Comparative Example 1 | | | |
| 10% | 43.5 | 68.0 | 85.1 |
| 15% | 17.0 | 43.2 | 75.1 |
| Comparative Example 2 | | | |
| 10% | 0.0 | 27.3 | 73.1 |
| 15% | 0.0 | 9.4 | 51.8 |
| Comparative Example 3 | | | |
| 10% | 7.8 | 40.6 | 79.7 |
| 15% | 0.0 | 10.8 | 58.6 |

In the case of the formulation of Comparative Example 1 containing a drug microparticles containing polyethylene glycol and the outer layer alone, suppression of the initial stage dissolution was not attained even when 15% of the outer layer was coated, because dissolution rate after 1 minute of the commencement of the dissolution test was 17.0% and the dissolution rate after 3 minutes was 43.2%, while suppression of the initial stage dissolution was markedly attained in the case of the formulation of Comparative Example 2 containing a drug microparticles containing hydroxypropylmethylcellulose and the outer layer alone, because dissolution rate after 1 minute of the commencement of the dissolution test was 0.0% and the dissolution rate after 3 minutes was 27.3% when 10% of the outer layer was coated, and when 15% of the outer layer was coated, dissolution rate after 1 minute of the commencement of the dissolution test was 0.0% and the dissolution rate after 3 minutes was 9.4%. In addition, suppression of the initial stage dissolution was markedly attained in the case of the formulation of Comparative Example 3 containing drug microparticles containing hydroxypropylcellulose and the outer layer alone, because dissolution rate after 1 minute of the commencement of the dissolution test was 0.0% and the dissolution rate after 3 minutes was 10.8% when 15% of the outer layer was coated. Based on the above results, initial stage dissolution of the drug microparticles containing hydroxypropylmethylcellulose or hydroxypropylcellulose can be suppressed by the coating with a general dissolution suppression layer, but initial stage dissolution of the drug microparticles containing polyethylene glycol is difficult to attain, and it was revealed that this is due to the polyethylene glycol used in the preparation of drug microparticles.

Test Example 2

Dissolution Test of Drug-Containing Coated Microparticles

The drug-containing coated microparticles obtained in Comparative Example 1 and Comparative Example 4 were respectively weighed in such a manner that the amount as solifenacin succinate became 5 mg, and the dissolution test was carried out in accordance with the second method of the dissolution test method of The Pharmacopoeia of Japan using a six-consecutive automatic dissolution tester (manufactured by Toyama Sangyo). As the test liquid, 900 ml of pH 6.8 phosphate buffer (the second liquid of the disintegration test method of The Pharmacopoeia of Japan) was used. This was carried out at a number of paddle rotation of 50 rotations/minute (Table 2).

TABLE 2

Dissolution test results of Comparative Example 1 and Comparative Example 4

| Outer layer coating ratio | 1 minute | 3 minutes | 30 minutes |
|---|---|---|---|
| Comparative Example 1 | | | |
| 10% | 43.5 | 68.0 | 85.1 |
| 15% | 17.0 | 43.2 | 75.1 |
| Comparative Example 4 | | | |
| 10% | 0.4 | 29.7 | 83.4 |
| 15% | 0.0 | 13.6 | 79.5 |

In the case of the formulation of Comparative Example 1 containing a drug microparticles containing polyethylene glycol and the outer layer alone, suppression of the initial stage dissolution was not attained even when 15% of the outer layer was coated, because dissolution rate after 1 minute of the commencement of the dissolution test was 17.0% and the dissolution rate after 3 minutes was 43.2%, while suppression of the initial stage dissolution was markedly attained in the case of the formulation of Comparative Example 4 in which the drug microparticles was coated with hydroxypropylmethylcellulose and further coated with ethyl cellulose/hydroxypropylmethylcellulose, because dissolution rate after 1 minute of the commencement of the dissolution test was 0.4% and the dissolution rate after 3 minutes was 29.7% when 10% of the outer layer was coated, and when 15% of the outer layer was coated, dissolution rate after 1 minute of the commencement of the dissolution test was 0.0% and the dissolution rate after 3 minutes was 13.6%, so that a pharmaceutical preparation which markedly attained suppression of initial dissolution and attained sufficient suppression of drug dissolution in the oral cavity was obtained. Based on this, it was shown that application of coating of hydroxypropylmethylcellulose and ethyl cellulose/hydroxypropylmethylcellulose to a drug microparticles is markedly effective when dissolution suppression is carried out on a particle which is extremely difficult to effect dissolution suppression such as a case of a drug microparticles containing polyethylene glycol or the like. However, it was unable to simultaneously attain initial stage dissolution suppression and a dissolution rate of 80% after 30 minutes of the commencement of the dissolution test, which is necessary for not reducing the bioavailability.

Test Example 3

Dissolution Test and Sensory Test of Drug-Containing Coated Microparticles

The drug-containing coated microparticles obtained in Comparative Example 1 and Comparative Example 5 were respectively weighed in such a manner that the amount as solifenacin succinate became 5 mg, and the dissolution test was carried out in accordance with the second method of the dissolution test method of The Pharmacopoeia of Japan using a six-consecutive automatic dissolution tester (manufactured by Toyama Sangyo). As the test liquid, 900 ml of pH 6.8 phosphate buffer (the second liquid of the disintegration test method of The Pharmacopoeia of Japan) was used. This was carried out at a number of paddle rotation of 100 rotations/minute (Table 3).

TABLE 3

Dissolution test results of Comparative Example 1 and Comparative Example 5

| Outer layer coating ratio | 1 minute | 3 minutes | 30 minutes |
|---|---|---|---|
| Comparative Example 1 | | | |
| 15% | 20.9 | 60.3 | 87.1 |
| Comparative Example 5 | | | |
| 13% | 0.0 | 26.1 | 80.2 |
| 14% | 0.0 | 23.4 | 79.1 |
| 15% | 0.0 | 16.5 | 74.0 |
| 16% | 0.0 | 15.8 | 72.5 |
| 17% | 0.0 | 11.9 | 70.7 |

In the case of the formulation of Comparative Example 1 containing a drug microparticles containing polyethylene glycol and the coat of ethyl cellulose/hydroxypropylmethylcellulose alone, suppression of the initial stage dissolution was not attained even when 15% of the outer layer was coated, because dissolution rate after 1 minute of the commencement of the dissolution test was 20.9% and the dissolution rate after 3 minutes was 60.3%, while suppression of the initial stage dissolution was markedly attained in the case of the formulation of Comparative Example 5 in which coating of hydroxypropylmethylcellulose and ethyl cellulose/hydroxypropylmethylcellulose was applied to the drug microparticles, because dissolution rate after 1 minute of the commencement of the dissolution test was 0.0% and the dissolution rate after 3 minutes was 16.5% when 15% of the outer layer was coated.

In addition, the drug-containing coated microparticles obtained in Comparative Example 1 (15% coating) and Comparative Example 5 (16% coating) were respectively weighed in such a manner that the amount as solifenacin succinate became 10 mg, and administered to three healthy volunteers to carry out a sensory test. In the test, respective drug-containing coated microparticles were held in the mouth and then spat out 1 minute thereafter, and the bitterness and astringency after their taking were periodically evaluated (Table 4).

TABLE 4

Sensory test results of drug-containing coated microparticles (n = 3)

| Evaluation time (min) | Comparative Example 1 (15% coating) | | Comparative Example 5 (16% coating) | |
|---|---|---|---|---|
| | Bitterness | Astringency | Bitterness | Astringency |
| 0.5 | ++, +, + | +, +, + | −, −, − | −, −, − |
| 1.0 | ++, ++, ++ | ++, ++, + | −, −, − | −, −, − |
| 1.5 | ++, ++, ++ | ++, ++, ± | ±, ±, − | −, −, − |
| 2 | ++, ++, ++ | ++, ++, ± | ±, ±, − | −, −, − |
| 3 | ++, ++, + | ++, ++, ± | ±, ±, ± | −, −, − |
| 5 | ++, ++, + | ++, ++, ± | −, ±, − | −, −, − |
| 7 | +, +, + | +, +, ± | −, −, − | −, −, − |

Evaluation of bitterness and astringency:
− (not felt),
± (slightly felt but no problem),
+ (felt),
++ (strongly felt)

As shown in Table 4, bitterness was hardly felt and astringency was not felt by the drug-containing coated microparticles prepared in Comparative Example 5, while strong bitterness was felt until 5 minutes after commencement of the administration, astringency was felt after commencement of the administration, and strong astringency was felt from 1 minute to 5 minutes after commencement of the administration, by the drug-containing coated microparticles prepared in Comparative Example 1. From the above results, it was shown that application of coating of hydroxypropylmethylcellulose and ethyl cellulose/hydroxypropylmethylcellulose is markedly effective when dissolution suppression is carried out on a particle which is extremely difficult to effect dissolution suppression such as a case of a drug microparticles containing polyethylene glycol or the like. However, it was unable to simultaneously attain initial stage dissolution suppression and a dissolution rate of 80% after 30 minutes of the commencement of the dissolution test.

Test Example 4

Dissolution Test of Drug-Containing Coated Microparticles

The drug-containing coated microparticles obtained in Example 2 and Comparative Example 6 were respectively weighed in such a manner that the amount as solifenacin succinate became 5 mg, and the dissolution test was carried out in accordance with the second method of the dissolution test method of The Pharmacopoeia of Japan using a six-consecutive automatic dissolution tester (manufactured by Toyama Sangyo). As the test liquid, 900 ml of pH 6.8 phosphate buffer (the second liquid of the disintegration test method of The Pharmacopoeia of Japan) was used. This was carried out at a number of paddle rotation of 100 rotations/minute (Table 2).

TABLE 2

Dissolution test results of Example 2 and Comparative Example 6

| Outer layer coating ratio | 1 minute | 3 minutes | 30 minutes |
|---|---|---|---|
| Example 2 | | | |
| 25% | 0.0 | 20.8 | 95.3 |
| 30% | 0.0 | 10.9 | 93.5 |
| Comparative Example 6 | | | |
| 25% | 2.7 | 44.2 | 92.5 |
| 30% | 0.0 | 32.6 | 96.2 |

In the case of the formulation of Comparative Example 6 containing a drug microparticles containing polyethylene glycol and the coat of ethyl cellulose/hydroxypropylcellulose alone, suppression of the initial stage dissolution was not attained at all even when 25% of the outer layer was coated, because dissolution rate after 1 minute of the commencement of the dissolution test was 2.7% and the dissolution rate after 3 minutes was 44.2%, and dissolution rate after 1 minute of the commencement of the dissolution test was 0.0% and the dissolution ratio after 3 minutes was 32.6% even when 30% of the outer layer was further coated, while significant suppression of the initial stage dissolution was attained in the case of the formulation of Example 2 in which coating of hydroxypropylmethylcellulose and ethyl cellulose/hydroxypropylmethylcellulose were applied to the drug microparticles, because dissolution rate after 1 minute of the commencement of the dissolution test was 0.0% and the dissolution rate after 3 minutes was 20.8% when 25% of the outer layer was coated, and when 30% of the outer layer was further coated, dissolution rate after 1 minute of the commencement of the dissolution test was 0.0% and the dissolution rate after 3 minutes was 10.9%, so that a pharmaceutical preparation which attained sufficient suppression of drug dissolution in the oral cavity was obtained. Based on this, it was shown that application of coating of hydroxypropylmethylcellulose and ethyl cellulose/hydroxypropylmethylcellulose to a drug microparticles is markedly effective when dissolution suppression is carried out on a particle which is extremely difficult to effect dissolution suppression such as a case of a drug microparticles containing polyethylene glycol or the like. In addition, it became possible for the first time to simultaneously attain initial stage dissolution suppression and a dissolution rate of 80% after 30 minutes of the commencement of the dissolution test, by employing said construction.

Test Example 5

Dissolution Test and Sensory Test of Drug-Containing Coated Microparticles

The drug-containing coated microparticles obtained in Example 1 were weighed in such a manner that the amount as solifenacin succinate became 5 mg, and the dissolution test was carried out in accordance with the second method of the dissolution test method of The Pharmacopoeia of Japan using a six-consecutive automatic dissolution tester (manufactured by Toyama Sangyo). As the test liquid, 900 ml of pH 6.8 phosphate buffer (the second liquid of the disintegration test method of The Pharmacopoeia of Japan) was used. This was carried out at a number of paddle rotation of 100 rotations/minute (Table 5).

TABLE 5

Dissolution test results of Example 1
Example 1

| Outer layer coating ratio | 1 minute | 3 minutes | 30 minutes |
|---|---|---|---|
| 30% | 0.0 | 14.9 | 93.1 |

When 30% of the outer layer was coated, significant suppression of the initial stage dissolution was attained, because dissolution rate after 1 minute of the commencement of the dissolution test was 0.0% and the dissolution rate after 3 minutes was 14.9%, and quick dissolution at the latter stage was attained, because dissolution rate after 30 minute of the commencement of the dissolution test was 93.1%. In addition, the drug-containing coated microparticles obtained in Example 1 (30% coating) were weighed in such a manner that the amount as solifenacin succinate became 10 mg, and administered to 3 healthy volunteers to carry out a sensory test. In the test, the drug-containing coated microparticles were held in the mouth and then spat out 1 minute thereafter, and the bitterness and astringency after their taking were periodically evaluated (Table 6).

TABLE 6

Sensory test results of drug-containing coated microparticles (n = 3)

| Evaluation time (min) | Example 1 (30% coating) | |
|---|---|---|
| | Bitterness | Astringency |
| 0.5 | −, −, − | −, −, − |
| 1.0 | −, ±, − | −, −, − |

TABLE 6-continued

Sensory test results of drug-containing coated microparticles (n = 3)

| Evaluation time (min) | Example 1 (30% coating) | |
|---|---|---|
| | Bitterness | Astringency |
| 1.5 | −, ±, ± | −, −, − |
| 2 | −, −, ± | −, −, − |
| 3 | ±, −, ± | −, −, − |
| 5 | −, −, − | −, −, − |
| 7 | −, −, − | −, −, − |

Evaluation of bitterness and astringency:
− (not felt),
± (slightly felt but no problem),
+ (felt),
++ (strongly felt)

As shown in Table 6, bitterness was hardly felt and astringency was not felt at all by the drug-containing coated microparticles prepared in Example 1. Based on the above, it was considered that a pharmaceutical preparation which simultaneously attained sufficient suppression of drug dissolution in the oral cavity and quick drub dissolution in the gastrointestinal tract was obtained.

Test Example 6

Oral Administration Test of Drug-Containing Coated Microparticles to Beagle Dog

The drug-containing coated microparticles obtained in Example 1 or Comparative Example 5 were orally administered to 7 animals (males) of beagle dog under a fasting condition, together with 20 ml of water in such a manner that the amount as solifenacin succinate became 10 mg/kg. The blood collecting time was set to 0.25, 0.5, 1, 2, 3, 4, 6, 8 and 10 hours, and the solifenacin succinate concentration in blood plasma was measured by an HPLC method. As a control, a solifenacin succinate aqueous solution was administered under the fasting condition in such a manner that the amount as solifenacin succinate became 10 mg/kg.

Regarding the administered drug-containing coated microparticles, those in which the outer layer was 30% coated were administered in the case of Example 1, and those in which the dissolution suppression layer was 14% coated in the case of Comparative Example 5. Dissolution rate of the drug-containing coated microparticles are shown in Table 7. The dissolution test was carried out in accordance with the second method of the dissolution test method of The Pharmacopoeia of Japan using a six-consecutive automatic dissolution tester (manufactured by Toyama Sangyo) after weighing in such a manner that the amount as solifenacin succinate became 5 mg. As the test liquid, 900 ml of pH 6.8 phosphate buffer (the second liquid of the disintegration test method of The Pharmacopoeia of Japan) was used. This was carried out at a number of paddle rotation of 100 rotations/minute.

TABLE 7

Dissolution test results of drug-containing coated microparticles of Example 1 and Comparative Example 5 orally administered to beagle dog

| Outer layer coating ratio | 1 minute | 3 minutes | 30 minutes |
|---|---|---|---|
| Example 1 | | | |
| 30% | 0.0 | 14.9 | 93.1 |
| Comparative Example 5 | | | |
| 14% | 0.0 | 23.4 | 79.1 |

The obtained changes in the plasma concentration of solifenacin succinate are shown in FIG. 1.

In the case of the drug-containing coated microparticles of Example 1 wherein the dissolution ratio after 30 minutes was 80% or more (93.1%), significant differences in the Cmax and AUC were not found in comparison with the aqueous solution administration, but in the case of the drug-containing coated microparticles of Comparative Example 5 wherein the dissolution ratio after 30 minutes was 80% or less (79.1%), significant difference in the AUC was found in comparison with the aqueous solution administration (59% against AUC at the time of aqueous solution administration). From the above results, it was confirmed that a dissolution rate of 80% or more after 30 minutes is necessary for attaining quick dissolution in the gastrointestinal tract.

Test Example 7

Dissolution Test of Drug-Containing Coated Microparticles

The drug-containing coated microparticles obtained in Example 2 and Example 3 were respectively weighed in such a manner that the amount as solifenacin succinate became 5 mg, and the dissolution test was carried out in accordance with the second method of the dissolution test method of The Pharmacopoeia of Japan using a six-consecutive automatic dissolution tester (manufactured by Toyama Sangyo). As the test liquid, 900 ml of pH 6.8 phosphate buffer (the second liquid of the disintegration test method of The Pharmacopoeia of Japan) was used. This was carried out at a number of paddle rotation of 100 rotations/minute (Table 8).

TABLE 8

Dissolution test results of Example 2 and Example 3

| Outer layer coating ratio | 1 minute | 3 minutes | 30 minutes |
|---|---|---|---|
| Example 2 | | | |
| 25% | 0.0 | 20.8 | 95.3 |
| 30% | 0.0 | 10.9 | 93.5 |
| 35% | 0.0 | 1.1 | 86.2 |
| 40% | 0.0 | 0.0 | 82.2 |
| Example 3 | | | |
| 40% | 0.3 | 19.9 | 96.8 |
| 45% | 1.2 | 18.4 | 96.5 |
| 55% | 0.0 | 10.0 | 98.1 |
| 60% | 0.0 | 5.5 | 90.9 |

In each of the invention formulations, it was shown that a pharmaceutical preparation capable of attaining suppression of early stage dissolution (from 0% to 3% 1 minute after the commencement of the dissolution test, from 0% to 25% after 3 minutes) and acceleration of latter stage dissolution (80% or more after 30 minutes) can be obtained, namely a pharmaceutical preparation capable of simultaneously achieving sufficient suppression of drug dissolution in the oral cavity and quick drug dissolution in the gastrointestinal tract can be obtained.

Test Example 8

Dissolution Test of Drug-Containing Coated Microparticles

The drug-containing coated microparticles obtained in Example 4 and Example 5 were respectively weighed in such a manner that the amount as solifenacin succinate became 5 mg, and the dissolution test was carried out in accordance with the second method of the dissolution test method of The Pharmacopoeia of Japan using a six-consecutive automatic dissolution tester (manufactured by Toyama Sangyo). As the test liquid, 900 ml of pH 6.8 phosphate buffer (the second liquid of the disintegration test method of The Pharmacopoeia of Japan) was used. This was carried out at a number of paddle rotation of 100 rotations/minute (Table 9).

TABLE 9

Dissolution test results of Example 4 and Example 5

| Outer layer coating ratio | 1 minute | 3 minutes | 30 minutes |
|---|---|---|---|
| Example 4 | | | |
| 45% | 0.0 | 19.4 | 91.5 |
| 50% | 0.0 | 9.9 | 89.7 |
| Example 5 | | | |
| 25% | 0.0 | 23.0 | 93.3 |
| 30% | 0.0 | 11.4 | 93.4 |
| 35% | 0.0 | 4.4 | 84.7 |

In each of the invention formulations, it was shown that a pharmaceutical preparation capable of attaining suppression of early stage dissolution (from 0% to 3% 1 minute after the commencement of the dissolution test, from 0% to 25% after 3 minutes) and acceleration of latter stage dissolution (80% or more after 30 minutes) can be obtained, namely a pharmaceutical preparation capable of simultaneously attaining sufficient suppression of drug dissolution in the oral cavity and quick drug dissolution in the gastrointestinal tract can be obtained.

Test Example 9

Dissolution Test of Drug-Containing Coated Microparticles

The drug-containing coated microparticles obtained in Example 2, Example 6 and Comparative Example 7 were respectively weighed in such a manner that the amount as solifenacin succinate became 5 mg, and the dissolution test was carried out in accordance with the second method of the dissolution test method of The Pharmacopoeia of Japan using a six-consecutive automatic dissolution tester (manufactured by Toyama Sangyo). As the test liquid, 900 ml of pH 6.8 phosphate buffer (the second liquid of the disintegration test method of The Pharmacopoeia of Japan) was used. This was carried out at a number of paddle rotation of 100 rotations/minute (Table 10).

TABLE 10

Dissolution test results of Example 2, Example 6 and Comparative Example 7

| Outer layer coating ratio | 1 minute | 3 minutes | 30 minutes |
|---|---|---|---|
| Example 2 | | | |
| 25% | 0.0 | 20.8 | 95.3 |
| 30% | 0.0 | 10.9 | 93.5 |
| 35% | 0.0 | 1.1 | 86.2 |
| 40% | 0.0 | 0.0 | 82.2 |
| Example 6 | | | |
| 40% | 0.0 | 15.1 | 92.9 |
| 45% | 0.0 | 10.3 | 96.9 |
| 50% | 0.0 | 5.4 | 93.5 |
| Comparative Example 7 | | | |
| 5% | 46.7 | 84.0 | 99.4 |
| 10% | 19.0 | 61.4 | 100.7 |
| 15% | 6.1 | 41.3 | 99.9 |
| 20% | 3.9 | 28.2 | 91.5 |
| 25% | 0.0 | 8.3 | 70.8 |
| 30% | 0.0 | 2.9 | 61.5 |

In each of Example 2 and Example 6 respectively having the ratio of ethyl cellulose and hydroxypropylcellulose of the dissolution suppression layer of 75/25 and 70/30, it was shown that a pharmaceutical preparation capable of attaining suppression of early stage dissolution (from 0% to 3% 1 minute after the commencement of the dissolution test, from 0% to 25% after 3 minutes) and acceleration of latter stage dissolution (80% or more after 30 minutes) can be obtained by adjusting coating amount of the outer layer, namely a pharmaceutical preparation capable of simultaneously attaining sufficient suppression of drug dissolution in the oral cavity and quick drug dissolution in the gastrointestinal tract can be obtained. On the other hand, in the Comparative Example 7 having the ratio of ethyl cellulose and hydroxypropylcellulose of the dissolution suppression layer of 79/21, it was unable to simultaneously attain the initial stage dissolution suppression and the 80% dissolution rate 30 minutes after the commencement of the dissolution test. Based on the above, it was shown that the ratio of ethyl cellulose occupying the dissolution suppression layer to the drug-containing microparticles containing solifenacin succinate and polyethylene glycol must be lower than 79%.

Test Example 10

Dissolution Test of Quickly Disintegrating Tablets in the Oral Cavity Containing Drug-Containing Coated Microparticles The quickly disintegrating tablets in the oral cavity containing drug-containing coated microparticles, obtained in Example 7 or Example 8, was weighed in such a manner that the amount as solifenacin succinate became 10 mg, and the dissolution test was carried out in accordance with the second method of the dissolution test method of The Pharmacopoeia of Japan using a six-consecutive automatic dissolution tester (manufactured by Toyama Sangyo). As the test liquid, 900 ml of pH 6.8 phosphate buffer (the second liquid of the disintegration test method of The Pharmacopoeia of Japan) was used. This was carried out at a number of paddle rotation of 100 rotations/minute (Table 11).

TABLE 11

Dissolution test results of Example 7 and Example 8

| quickly disintegrating tablet | 1 min | 3 min | 30 min |
|---|---|---|---|
| Example 7 | | | |
| WOW 1 | 0.0 | 17.4 | 95.4 |
| Example 8 | | | |
| WOW 2 | 1.5 | 11.8 | 93.8 |

In each of the quickly disintegrating tablets in the oral cavity, it was shown that a pharmaceutical preparation capable of attaining suppression of early stage dissolution (from 0% to 3% 1 minute after the commencement of the dissolution test, from 0% to 25% after 3 minutes) and acceleration of latter stage dissolution (80% or more after 30 minutes) can be obtained, namely a pharmaceutical preparation capable of simultaneously attaining sufficient suppression of drug dissolution in the oral cavity and quick drug dissolution in the gastrointestinal tract can be obtained.

INDUSTRIAL APPLICABILITY

It is possible to apply the present invention also to various drugs. Particularly, the conflicting issues of suppressing unpleasant taste of a drug having very bitter taste, a drug having astringency and the like in the oral cavity and of effecting quick drug dissolution in the gastrointestinal tracts, which have so far been difficult to achieve, were simultaneously achieved for the first time by selecting a construction of coating a specified water-soluble polymer and a specified mixing ratio of a water-insoluble polymer and hydroxypropylcellulose, and this fact exerts an effect of greatly expanding applicability of such drugs to quickly disintegrating preparations in the oral cavity.

The invention claimed is:

1. Drug containing coated microparticles having an average particle diameter of 350 μm or less, for quickly disintegrating preparations in the oral cavity, wherein microparticles containing the drug solifenacin or a salt thereof and polyethylene glycol which are present in a homogeneously mixed state are coated with a film comprising a water-soluble polymer, said water-soluble polymer selected from the group consisting of hydroxypropylmethylcellulose, hydroxypropylcellulose, methyl cellulose and a mixture thereof, and are further coated with an outer film comprising:
  (1) a pH-independent water-insoluble polymer accounting for 60% or more and less than 79% of the film, wherein the pH-independent water-insoluble polymer is ethyl cellulose; and
  (2) hydroxypropylcellulose accounting for more than 21% and 40% or less of the film, wherein the rate of dissolution of drug from the drug-containing coated microparticles using a test liquid simulating inside of the oral cavity is from 0% to 25% in 3 minutes.

2. The drug-containing coated microparticles for use in quickly disintegrating preparations in the oral cavity described in claim 1, wherein the water-soluble polymer is hydroxypropylmethylcellulose.

3. The drug-containing coated microparticles for use in quickly disintegrating preparations in the oral cavity described in any of claim 1 or 2, wherein rate of dissolution of drug from the drug-containing coated microparticles using a test liquid simulating inside of the oral cavity is from 0% to 3% in 1 minute and from 0% to 25% in 3 minutes, and rate of dissolution of drug from the drug-containing coated microparticles using a test liquid simulating inside the gastrointestinal tract is 80% or more in 30 minutes.

4. A method for producing drug-containing coated microparticles having an average particle diameter of 350 μm or less, for quickly disintegrating preparations in the oral cavity, wherein microparticles containing the drug solifenacin or a salt thereof and polyethylene glycol which are present in a homogeneously mixed state are coated with a film comprising a water-soluble polymer, said water-soluble polymer selected from the group consisting of hydroxypropylmethylcellulose, hydroxypropylcellulose, methyl cellulose and a mixture thereof, and are further coated with an outer film comprising:
  (1) a pH-independent water-insoluble polymer accounting for 60% or more and less than 79% of the film, wherein the pH-independent water-insoluble polymer is ethyl cellulose; and
  (2) hydroxypropylcellulose accounting for more than 21% and 40% or less of the film, wherein the rate of dissolution of drug from the drug-containing coated microparticles using a test liquid simulating inside of the oral cavity is from 0% to 25% in 3 minutes.

5. A quickly disintegrating preparation in the oral cavity containing drug-containing coated microparticles having an average particle diameter of 350 μm or less, for quickly disintegrating preparations in the oral cavity, wherein microparticles containing the drug solifenacin or a salt thereof and polyethylene glycol which are present in a homogeneously mixed state are coated with a film comprising a water-soluble polymer, said water-soluble polymer selected from the group consisting of hydroxypropylmethylcellulose, hydroxypropylcellulose, methyl cellulose and a mixture thereof, and are further coated with an outer film comprising:
  (1) a pH-independent water-insoluble polymer accounting for 60% or more and less than 79% of the film, wherein the pH-independent water-insoluble polymer is ethyl cellulose; and
  (2) hydroxypropylcellulose accounting for more than 21% and 40% or less of the film, wherein the rate of dissolution of drug from the drug-containing coated microparticles using a test liquid simulating inside of the oral cavity is from 0% to 25% in 3 minutes.

6. Drug-containing coated microparticles having an average particle diameter of 350 μm or less, for quickly disintegrating preparations in the oral cavity, wherein microparticles containing solifenacin succinate and polyethylene glycol which are present in a homogeneously mixed state are coated with a film comprising a water-soluble polymer, said water-soluble polymer selected from the group consisting of hydroxypropylmethylcellulose, hydroxypropylcellulose, methyl cellulose and a mixture thereof, and are further coated with an outer film comprising:
  (1) a pH-independent water-insoluble polymer accounting for 60% or more and less than 79% of the film, wherein the pH-independent water-insoluble polymer is ethyl cellulose; and
  (2) hydroxypropylcellulose accounting for more than 21% and 40% or less of the film, wherein the rate of dissolution of drug from the drug-containing coated microparticles using a test liquid simulating inside of the oral cavity is from 0% to 25% in 3 minutes.

7. The drug-containing coated microparticles for use in quickly disintegrating preparations in the oral cavity described in claim 6, wherein the water-soluble polymer is hydroxypropylmethylcellulose.

8. The drug-containing coated microparticles for use in quickly disintegrating preparations in the oral cavity described in claim 6 or 7, wherein rate of dissolution of drug from the drug-containing coated microparticles using a test liquid simulating inside of the oral cavity is from 0% to 3% in 1 minute and from 0% to 25% in 3 minutes, and rate of dissolution of drug from the drug-containing coated microparticles using a test liquid simulating inside the gastrointestinal tract is 80% or more in 30 minutes.

9. A method for producing drug-containing coated microparticles having an average particle diameter of 350 μm or less, for quickly disintegrating preparations in the oral cavity, wherein microparticles containing solifenacin succinate and polyethylene glycol which are present in a homogeneously mixed state are coated with a film comprising a water-soluble polymer, said water-soluble polymer selected from the group consisting of hydroxypropylmethylcellulose, hydroxypropylcellulose, methyl cellulose and a mixture thereof, and are further coated with an outer film comprising:
   (1) a pH-independent water-insoluble polymer accounting for 60% or more and less than 79% of the film, wherein the pH-independent water-insoluble polymer is ethyl cellulose; and
   (2) hydroxypropylcellulose accounting for more than 21% and 40% or less of the film, wherein the rate of dissolution of drug from the drug-containing coated microparticles using a test liquid simulating inside of the oral cavity is from 0% to 25% in 3 minutes.

10. A quickly disintegrating preparation in the oral cavity containing drug-containing coated microparticles having an average particle diameter of 350 μm or less, for quickly disintegrating preparations in the oral cavity, wherein microparticles containing a drug and polyethylene glycol, said drug is solifenacin succinate, which are present in a homogeneously mixed state are coated with a film comprising a water-soluble polymer, said water-soluble polymer selected from the group consisting of hydroxypropylmethylcellulose, hydroxypropylcellulose, methyl cellulose and a mixture thereof, and are further coated with an outer film comprising:
   (1) a pH-independent water-insoluble polymer accounting for 60% or more and less than 79% of the film, wherein the pH-independent water-insoluble polymer is ethyl cellulose; and
   (2) hydroxypropylcellulose accounting for more than 21% and 40% or less of the film, wherein the rate of dissolution of drug from the drug-containing coated microparticles using a test liquid simulating inside of the oral cavity is from 0% to 25% in 3 minutes.

11. The drug-containing coated microparticles for use in quickly disintegrating preparations in the oral cavity of claim 1 or 6, wherein the water-soluble polymer is hydroxypropylcellulose.

12. The drug-containing coated microparticles for use in quickly disintegrating preparations in the oral cavity of claim 1 or 6, wherein the water-soluble polymer is methyl cellulose.

13. A method for producing drug-containing coated microparticles having an average particle diameter of 350 μm or less, for quickly disintegrating preparations in the oral cavity of claim 4 or 9, wherein the water-soluble polymer is hydroxypropylmethylcellulose.

14. A method for producing drug-containing coated microparticles having an average particle diameter of 350 μm or less, for quickly disintegrating preparations in the oral cavity of claim 4 or 9, wherein the water-soluble polymer is hydroxypropylcellulose.

15. A method for producing drug-containing coated microparticles having an average particle diameter of 350 μm or less, for quickly disintegrating preparations in the oral cavity of claim 4 or 9, wherein the water-soluble polymer is methyl cellulose.

16. A quickly disintegrating preparation in the oral cavity containing drug-containing coated microparticles having an average particle diameter of 350 μm or less, for quickly disintegrating preparations in the oral cavity of claim 5 or 10, wherein the water-soluble polymer is hydroxypropylmethylcellulose.

17. A quickly disintegrating preparation in the oral cavity containing drug-containing coated microparticles having an average particle diameter of 350 μm or less, for quickly disintegrating preparations in the oral cavity of claim 5 or 10, wherein the water-soluble polymer is hydroxypropylcellulose.

18. A quickly disintegrating preparation in the oral cavity containing drug-containing coated microparticles having an average particle diameter of 350 μm or less, for quickly disintegrating preparations in the oral cavity of claim 5 or 10, wherein the water-soluble polymer is methyl cellulose.

* * * * *